(12) United States Patent
Loboda et al.

(10) Patent No.: US 11,776,801 B2
(45) Date of Patent: Oct. 3, 2023

(54) INDUCTIVELY COUPLED PLASMA BASED ATOMIC ANALYSIS SYSTEMS AND METHODS

(71) Applicant: Fluidigm Canada Inc., Markham (CA)

(72) Inventors: Alexander Loboda, Thornhill (CA); Raymond Jong, Toronto (CA); Michael Sullivan, Ontario (CA); Serguei Vorobiev, Aurora (CA); Robert Rotenberg, Aurora (CA); Emil D. Stratulativ, Toronto (CA); Maxim Voronov, Markham (CA); Mark Armstrong, Toronto (CA)

(73) Assignee: STANDARD BIOTOOLS CANADA INC., Markham (CA)

(*) Notice: Subject to any disclaimer, the term of this patent is extended or adjusted under 35 U.S.C. 154(b) by 0 days.

(21) Appl. No.: 17/470,769

(22) Filed: Sep. 9, 2021

(65) Prior Publication Data

US 2022/0093382 A1  Mar. 24, 2022

Related U.S. Application Data

(60) Provisional application No. 63/184,521, filed on May 5, 2021, provisional application No. 63/081,172, filed (Continued)

(51) Int. Cl.
*H01J 49/00* (2006.01)
*H01J 49/10* (2006.01)
(Continued)

(52) U.S. Cl.
CPC ........ *H01J 49/105* (2013.01); *H01J 49/0027* (2013.01); *H01J 49/0463* (2013.01); *H05H 1/2406* (2013.01); *H05H 1/30* (2013.01)

(58) Field of Classification Search
CPC .. H01J 49/105; H01J 49/0027; H01J 49/0463; H05H 1/2406; H05H 1/30
(Continued)

(56) References Cited

U.S. PATENT DOCUMENTS

| | | | | | |
|---|---|---|---|---|---|
| 4,739,147 | A | * | 4/1988 | Meyer | H05H 1/30 219/121.36 |
| 6,166,379 | A | * | 12/2000 | Montaser | H01J 49/045 219/121.52 |

(Continued)

FOREIGN PATENT DOCUMENTS

| | | | | |
|---|---|---|---|---|
| KR | 101715340 B1 | * | 3/2017 | ............... H05H 1/46 |
| KR | 101715340 B1 | | 3/2017 | |

OTHER PUBLICATIONS

International Application No. PCT/US2021/049667 received an International Search Report and Written Opinion, dated Jan. 26, 2022, 12 pages.
(Continued)

*Primary Examiner* — Michael Maskell
(74) *Attorney, Agent, or Firm* — Kilpatrick Townsend & Stockton ILP

(57) ABSTRACT

Inductively coupled plasma (ICP) analyzers use an ICP torch to generate a plasma in which a sample is atomized an ionized. Analysis of the atomic ions can be performed by atomic analysis, such as mass spectrometry (MS) or atomic emission spectrometry (AES). Particle based ICP analysis includes analysis of particles such as cells, beads, or laser ablation plumes, by atomizing and ionizing particles in an ICP torch followed by atomic analysis. In mass cytometry, mass tags of particles are analyzed by mass spectrometry, such as by ICP-MS. Systems and methods of the subject application include one or more of: a demountable ICP torch holder assembly, an external ignition device; an ICP load
(Continued)

coil comprising an annular fin, particle suspension sample introduction fluidics, and ICP analyzers thereof.

20 Claims, 14 Drawing Sheets

Related U.S. Application Data on Sep. 21, 2020, provisional application No. 63/080,672, filed on Sep. 18, 2020.

(51) Int. Cl.
  *H05H 1/30* (2006.01)
  *H05H 1/24* (2006.01)
  *H01J 49/04* (2006.01)

(58) Field of Classification Search
  USPC .................................. 250/281, 288
  See application file for complete search history.

(56) References Cited

U.S. PATENT DOCUMENTS

| | | | | |
|---|---|---|---|---|
| 7,511,246 B2* | 3/2009 | Morrisroe | ............. | G01N 21/73 |
| | | | | 219/121.48 |
| 7,847,210 B2* | 12/2010 | Brezni | .................. | H05H 1/30 |
| | | | | 219/121.36 |
| 10,327,319 B1* | 6/2019 | Morrisroe | ............ | H05H 1/0037 |
| 2004/0072250 A1 | 4/2004 | Baranov et al. | | |
| 2005/0218319 A1 | 10/2005 | Bandura et al. | | |
| 2008/0003616 A1 | 1/2008 | Winnik et al. | | |
| 2009/0102385 A1 | 4/2009 | Wi | | |
| 2011/0272386 A1 | 11/2011 | Morrisroe | | |
| 2013/0181126 A1 | 7/2013 | Jong | | |
| 2014/0263203 A1 | 9/2014 | Morrisroe | | |
| 2014/0287953 A1 | 9/2014 | Günther et al. | | |
| 2016/0056031 A1 | 2/2016 | Loboda | | |
| 2016/0195466 A1 | 7/2016 | Loboda et al. | | |
| 2019/0317082 A1 | 10/2019 | Baranov et al. | | |
| 2020/0343083 A1* | 10/2020 | Patel | ....................... | H05H 1/30 |

OTHER PUBLICATIONS

International Application No. PCT/US2021/049667 received an Invitation to Pay Additional Fees and, Where Applicable, Protest Fee, dated Nov. 3, 2021, 2 pages.

Al-Halhouli, et al., "Passive Micromixers with Interlocking Semi-Circle and Omega-Shaped Modules: Experiments and Simulations", *Micromachines* 2015 ISSN 072-666x, Jul. 22, 2015, 16 pages.

Giesen, et al., "Highly multiplexed imaging of tumor tissues with subcellular resolution by mass cytometry", *Nature Methods*, vol. 11, No. 4, Apr. 2014, 9 pages.

* cited by examiner

INDUCTIVELY COUPLED PLASMA BASED ATOMIC ANALYSIS SYSTEMS AND METHODS

CROSS-REFERENCES TO RELATED APPLICATIONS

This application claims the benefit of priority to U.S. Provisional Application No. 63/080,672, filed Sep. 18, 2020; U.S. Provisional Application No. 63/081,172, filed Sep. 21, 2020; and U.S. Provisional Application No. 63/184,521, filed May 5, 2021, the entire contents of all of which are incorporated herein by reference for all purposes.

TECHNICAL FIELD

The field of the subject application relates to systems and methods for inductively coupled plasma (ICP) analysis, including for mass cytometry.

BACKGROUND

Inductively coupled plasma (ICP) analyzers use an ICP torch to generate a plasma in which a sample is atomized an ionized. Analysis of the atomic ions can be performed by atomic analysis, such as mass spectrometry (MS) or atomic emission spectrometry (AES). Particle based ICP analysis includes analysis of particles such as cells, beads, or laser ablation plumes, by atomizing and ionizing particles in an ICP torch followed by atomic analysis. In mass cytometry, mass tags of particles are analyzed by mass spectrometry, such as by ICP-MS.

SUMMARY

Systems and methods of the subject application include one or more of: a demountable ICP torch holder assembly, an external ignition device; an ICP load coil comprising an annular fin, particle suspension sample introduction fluidics, and ICP analyzers thereof.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
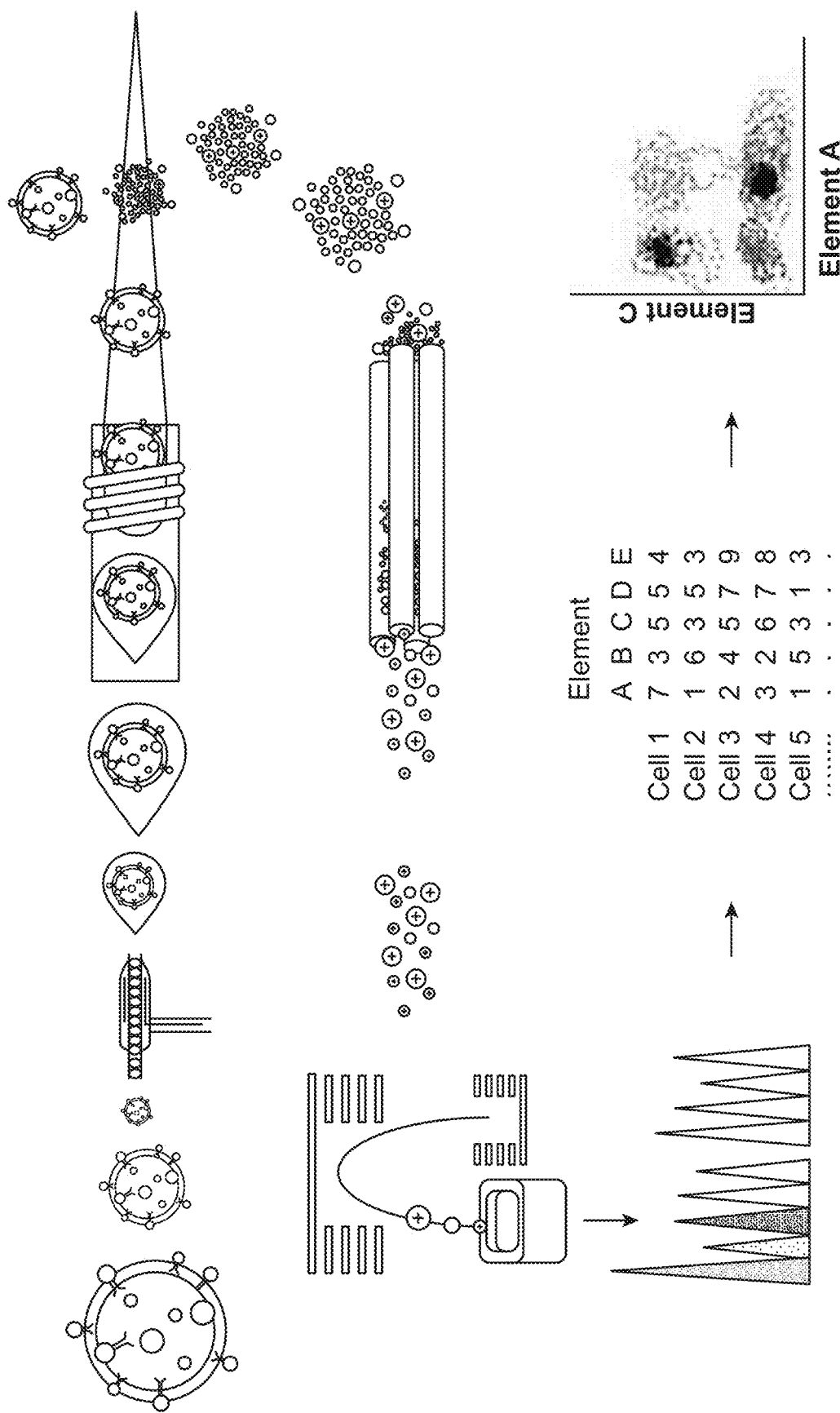
FIG. 1 is a schematic of a standard suspension mass cytometry workflow.

Certain aspects and features of the present disclosure relate to systems and methods for inductively coupled plasma (ICP) analysis, including for mass cytometry, as described further herein.

Inductively Coupled Plasma (ICP) Systems, Samples and Methods

An inductively coupled plasma (ICP) is a type of plasma source in which the energy is supplied by electric currents which are produced by electromagnetic induction (i.e., by time-varying magnetic fields). Industrial scale applications of ICP include micromachining (e.g., etching or cleaning) or waste disposal. Such applications may not generate plasma in an ICP torch, may not use an ICP load coil, may not operate under atmospheric conditions, and/or may not be at a scale suitable for atomic analysis of a sample (e.g., the plasma generated may be at least an order of magnitude larger that of ICP analyzers). As such, the physics of industrial ICP is different than for ICP analysis using an ICP torch, and may be outside the scope of aspects of the present disclosure. Discussed herein are systems and methods using ICP torches, such as ICP analyzers.

An overview of ICP mass spectrometers (ICP-MS) is provided in Montaser, Akbar, ed. *Inductively coupled plasma mass spectrometry*. John Wiley & Sons, 1998, which includes a description of vortex flow and ignition. Sample introduction and ICP torch considerations is similar for atomic emission spectroscopy (AES), also known as optical emission spectroscopy, which is also within the scope of the subject application. Atomic spectroscopy, as used herein, is identical to atomic analysis and may include atomic mass spectrometry (such as ICP-MS) or ICP-AES. Suitable samples include biological samples, geological samples, and articles of manufacture. In certain aspects, a biological sample may be a fluid comprising biomolecules and/or contaminants (e.g., metal toxins), or particles such as cell (e.g., in suspension or in a tissue section) or beads (e.g., used to assay biomolecules).

Mass Cytometry Systems and Methods

Aspects of the subject application include ICP-torch systems and methods for mass cytometry, which is the detection of mass tags in cells or beads by mass spectrometry. Mass cytometry is discussed in US patent publications US20050218319, US20160195466, and US20190317082, which are incorporated by reference in their entirety. Mass cytometry may be of suspended particles (e.g., cells or beads), or of particles produced from a solid sample, such as laser ablation plumes produced from a tissue section. In suspension mass cytometry, a suspension of cells or beads comprising mass tags are analyzed by atomic mass spectrometry. Imaging mass cytometry by laser ablation (LA) ICP-MS is described in US patent publications US20160056031 and US20140287953, which are incorporated herein by reference. Imaging mass cytometry by LA-ICP-MS is also described by Giesen, Charlotte, et al. in "Highly multiplexed imaging of tumor tissues with subcellular resolution by mass cytometry." (*Nature methods* 11.4 (2014): 417-422).

Mass tags may be metal tags bound to affinity reagents (e.g., antibodies, oligonucleotides, avidin, or other biomolecules that specifically bind a target biomolecule). For example, metal nanoparticles or metal-chelating polymers may be attached (e.g., covalently bound) to affinity reagents, which are then applied to the sample. Suitable mas tags are described in US patent publications US20040072250 and US20080003616, which are incorporated by reference in their entirety. In certain aspects, some mass tags are not coupled to affinity reagents, such as metal containing drugs or histochemical stains.

Figure 2:
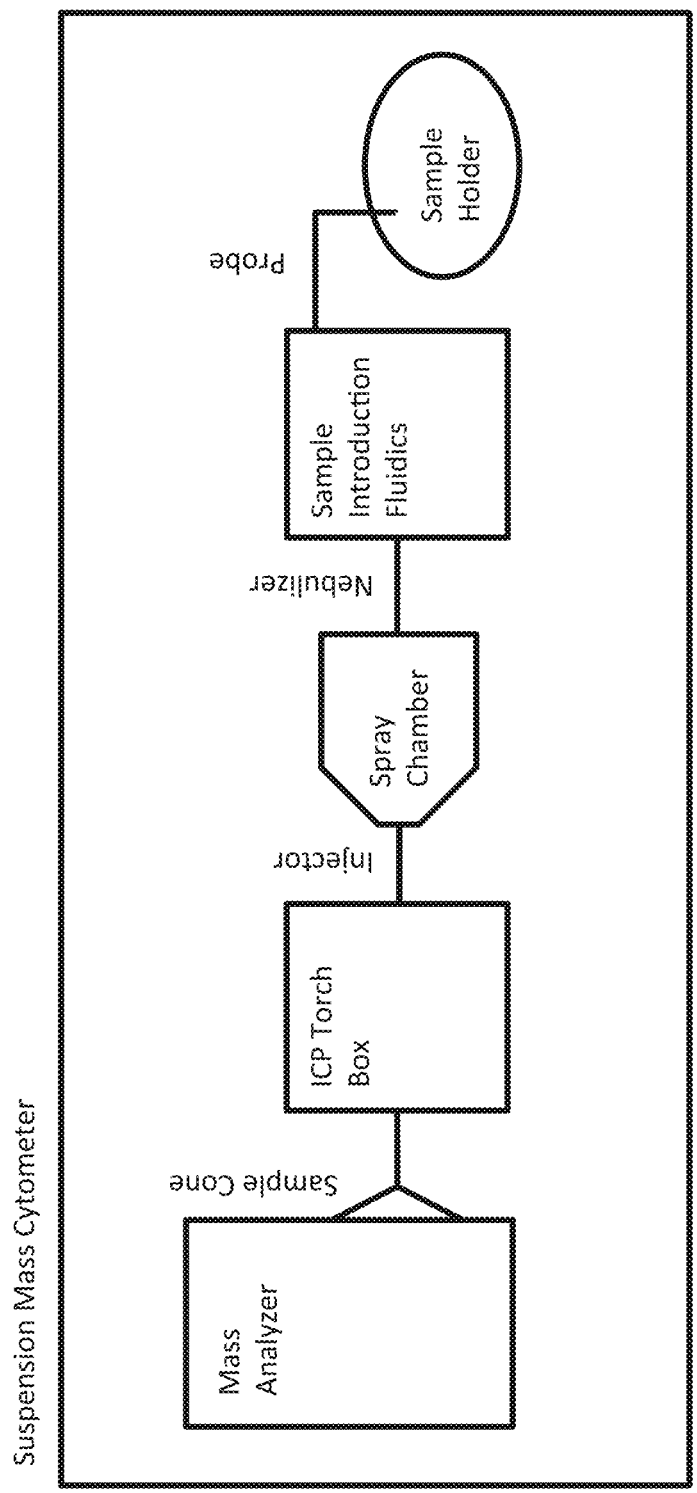
FIG. 2 is a diagram of a standard suspension mass cytometry system.

FIG. 1 is a schematic of a standard mass cytometry workflow, while FIG. 2 is a diagram of a standard mass cytometry system used in such a workflow. A suspension mass cytometry workflow may include labeling cells with mass tags (see cells labeled with tagged antibodies on upper left of FIG. 1). Particles, such as cells and/or beads, are transferred by sample introduction fluidics from a sample container (e.g., a tube) retained by a sample holder, through a nebulizer and into a spray chamber. The spray chamber passes a carrier gas (i.e., aerosol spray) around droplets expelled from the nebulizer. Unlike many other spray chambers, a spray chamber of a suspension mass cytometry system passes particles to an ICP torch box, rather than to a waste outlet. Exemplary spray chambers suitable for mass cytometry include spray chambers discussed by US patent publication US20130181126, which is incorporated by reference in its entirety. The ICP torch box, as described further herein, comprises an ICP torch. Particles pass into an ICP plasma of the ICP torch, where they are atomized and ionized. A vacuum differential directs ionized atoms from the plasma through a sample cone (and one or more additional cones) into a mass analyzer. Ion optics of the mass analyzer may, in some cases, be configured to filter ions. For example, when mass tags comprise heavy metals (such as transition elements or lanthanides), or isotopes thereof, a mass filter (such as a deflector or RF quadrupole) may be configured to act as a high pass mass filter and remove ions below a certain mass. As Argon dimer normally present in ICP plasma is 80 amu, a high pass mass filter may remove ions at a cutoff of at least 80 amu. Such a high pass filter may be particularly useful when the mass analyzer comprises a time-of-flight detector (i.e., is a TOF-MS). Suitable mass analyzers include simultaneous mass analyzers, such as TOF-MS or magnetic sector MS. In certain aspects, the mass analyzer may be another analyzer such as a quadrupole MS (QMS). Ions of mass tags that are detected by the mass analyzer indicate the presence of the target of the affinity reagent the mass tag specifically binds. As there is relatively little crosstalk between mass channels in mass cytometry compared to detection of fluorescent tags (which exhibit spectral overlap), a large number of mass tags may be distinguished in individual particles. In certain aspects, a plurality of distinguishable mass tags (e.g., at least 20, at least 30, or at least 40 mass tags) are detected in a single cell event.

In certain aspects, the system may comprise a filter positioned at an inlet to the nebulizer. The filter may allow single cells to pass through but may prevent clusters of cells from passing into the nebulizer, e.g., so as to reduce clogging at the nebulizer (such as at the tip of the nebulizer). The filter may comprise a mesh, such as a nylon mesh, or any material suitable for cell straining. The filter may allow passage of particles that are less than the inner diameter of a channel of the nebulizer, such as less than 80% or less than 50% of the inner diameter of the channel. For example, the nebulizer may have an inner diameter of 200 microns or less, 150 microns or less, or 100 microns or less, such as between 50 microns and 150 microns. The filter may have a cutoff that is above 25 microns, above 50 microns, above 80 microns, or above 100 microns, such that particles below the cutoff can pass into the nebulizer. The filter may be at the interface between a nebulizer and sample introduction fluidics shown in FIG. 2. The filter may be proximal to a sealed coupling between a sample loop of the sample introduction fluidics and the nebulizer. The inner diameter of the sample loop may be larger than the inner diameter of the channel of the nebulizer, such as at least 2 times or at least 5 times larger. For example, the inner diameter of the sample loop may be at least 0.2 mm, at least 0.5 mm, at least 1 mm, or at least 2 mm. The sealed coupling and/or the filter may be detachable from the nebulizer, e.g., so as to replace the filter.

While a mass cytometry workflow and system is described above, it is understood that a sampling system such as a laser ablation system may replace the sample introduction fluidics in order to deliver laser ablation plume particles to the mass cytometers.

ICP Torch Box

In general, and ICP torch box comprises an ICP torch body, an ICP load coil positioned around an outer tube of the torch body. Optionally further, an ICP torch box may include an ignition device and/or a gas supply manifold. The ICP torch body may include at least an inner tube and an outer tube, although the inner tube may be a middle tube positioned around an innermost tube. When the inner tube and outer tube are separable, they may be described as belonging to as separate inner tube body and outer tube body respectively. Embodiments of the invention include an ICP torch box, including specific devices and methods of using devices such as a ICP torch assembly (e.g., a demountable ICP torch holder assembly), external ignition device, ICP load coil, and/or gas supply manifold of any of the aspects described herein.

Figure 3:
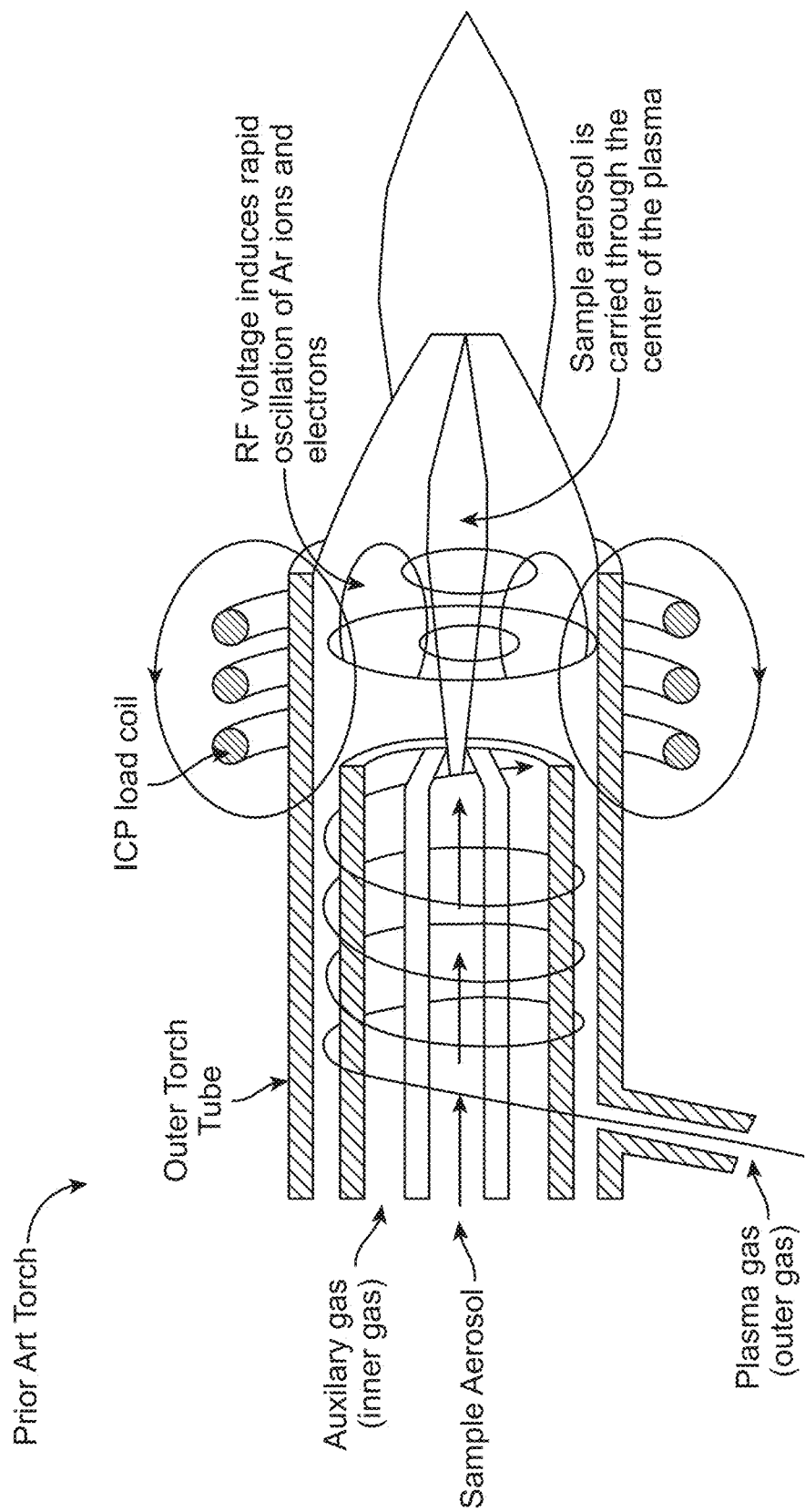
FIG. 3 is a diagram of a standard ICP torch.

As shown if FIG. 3, an exemplary torch of the art may provide a vortex flow with a single outer gas (i.e., plasma gas) inlet, or in some cases two inlets. The outer gas inlet may extend from the torch tube, and may be of the same material.

Figure 4:
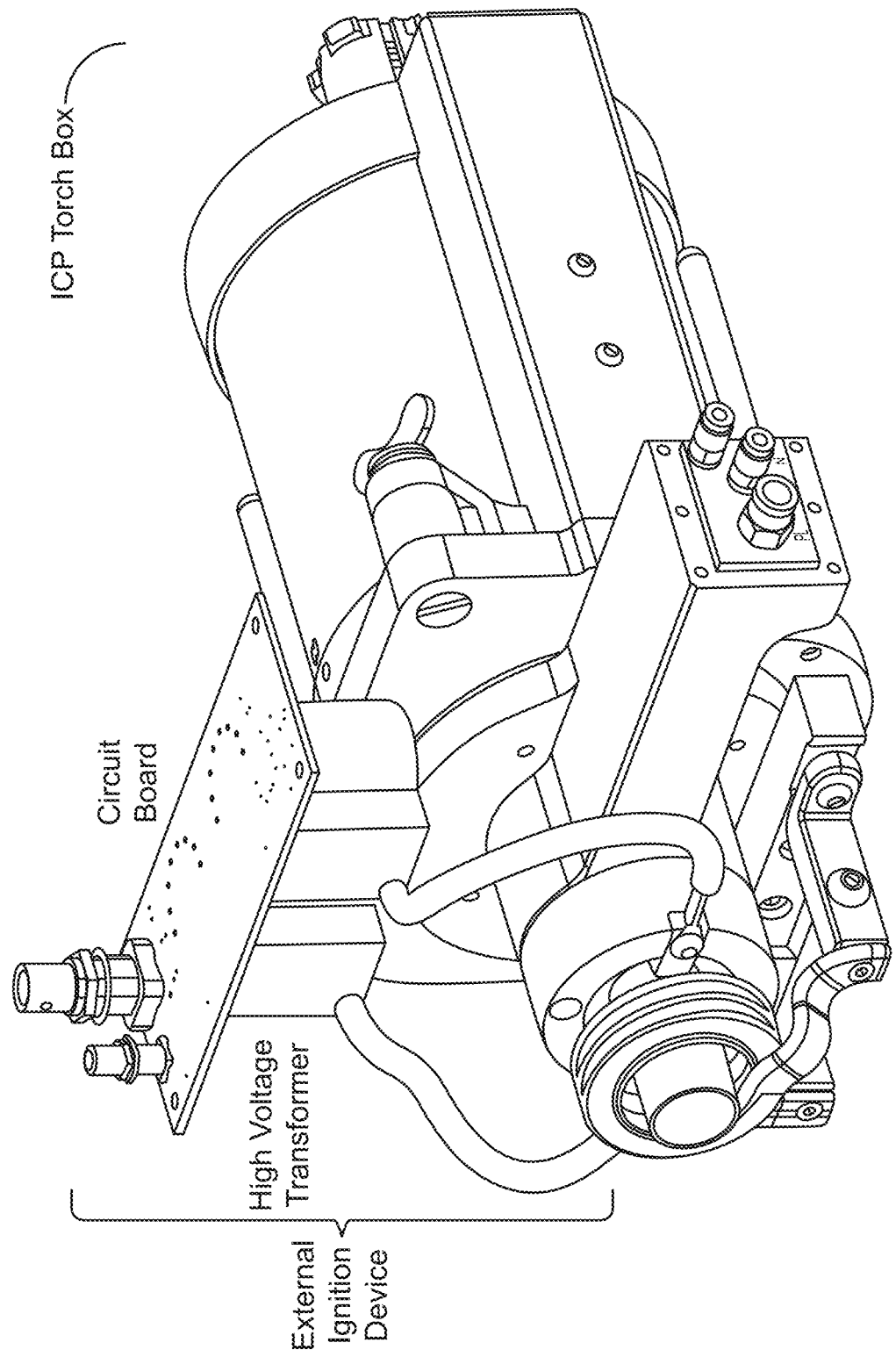
FIG. 4 is a diagram of an exemplary ICP torch box of the subject application.

An exemplary torch box of the subject application is shown in FIG. 4, which depicts an external ignition device comprising a circuit board comprising two high voltage transformers that provide an alternating output voltage to two electrodes positioned outside an outer torch tube. An exploded view of the rest of the torch box is provided in FIG. 5. An ICP load coil comprising an annular fin is shown to the left side of FIG. 5, as is a Gas Supply Manifold that retains a detachable torch holder assembly. A spray chamber is shown upstream of the torch box, and comprises an injector that extends into an inner tube of the torch assembly.

Figure 6:
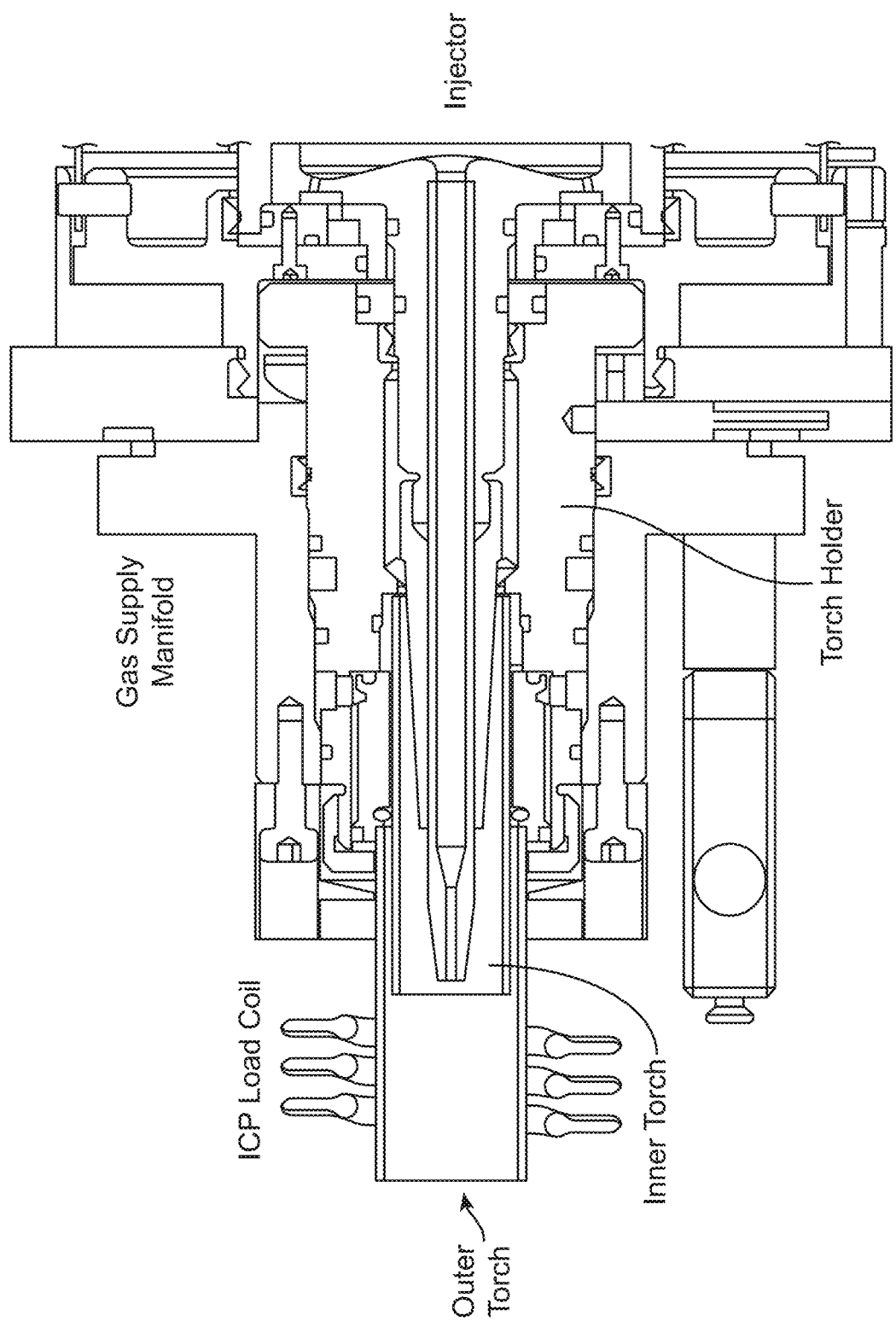
FIG. 6 is a cross section of an ICP torch box of FIG. 4.

FIG. 6 is a cross section of the torch assembly. Most elements continue radially around the axis of the injector and torch. The annular fin of the ICP load coil is shown to be thinner than it is long. The torch holder is shown to be positioned around the inner and outer torch body, and to be positioned within the gas supply manifold. As discussed further herein, gas flows from the manifold, through the torch holder, and into the inner or outer torch.

Figure 5:
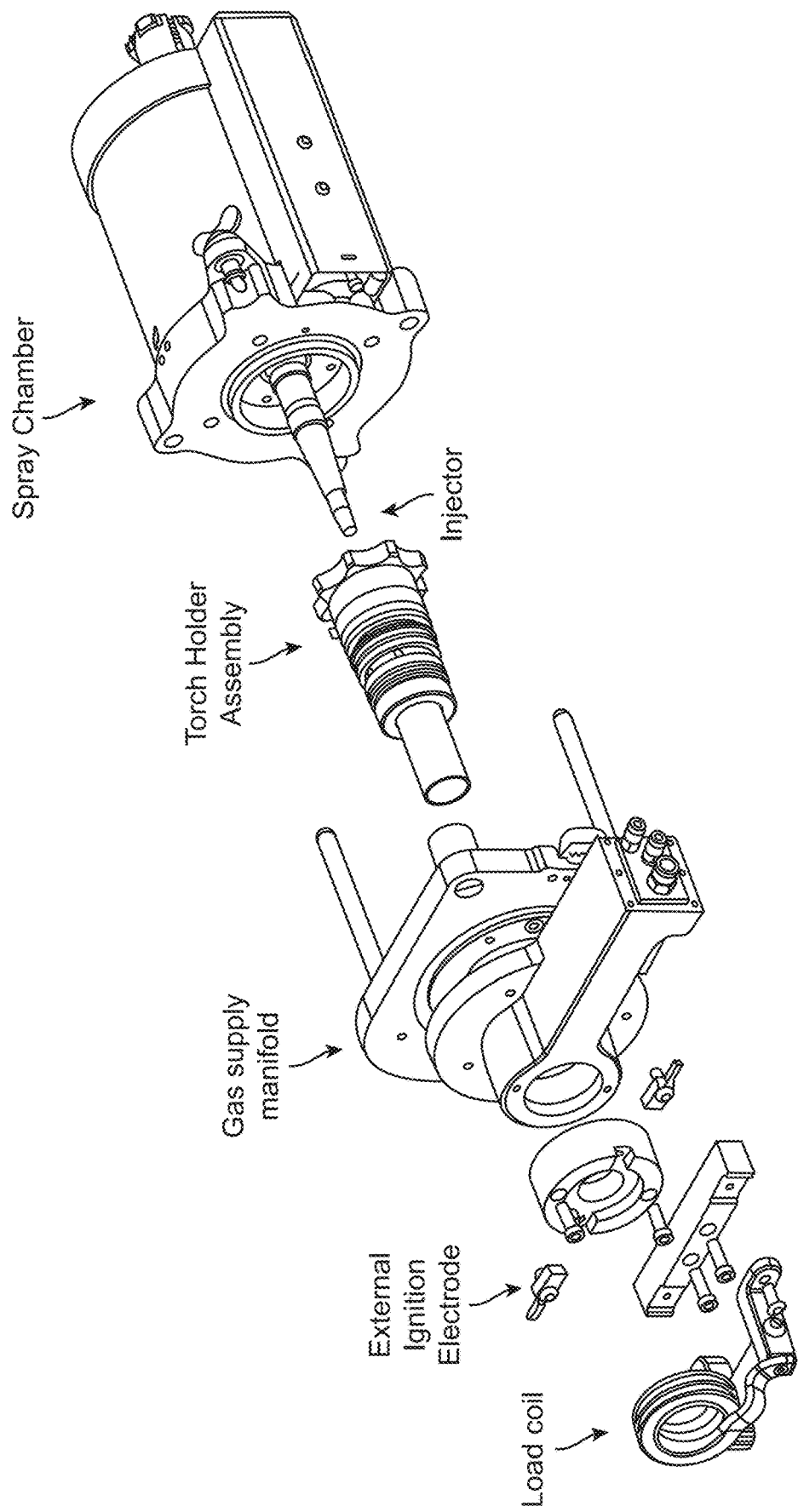
FIG. 5 is an exploded diagram of the ICP torch box of FIG. 4 and an upstream spray chamber.
Figure 7:
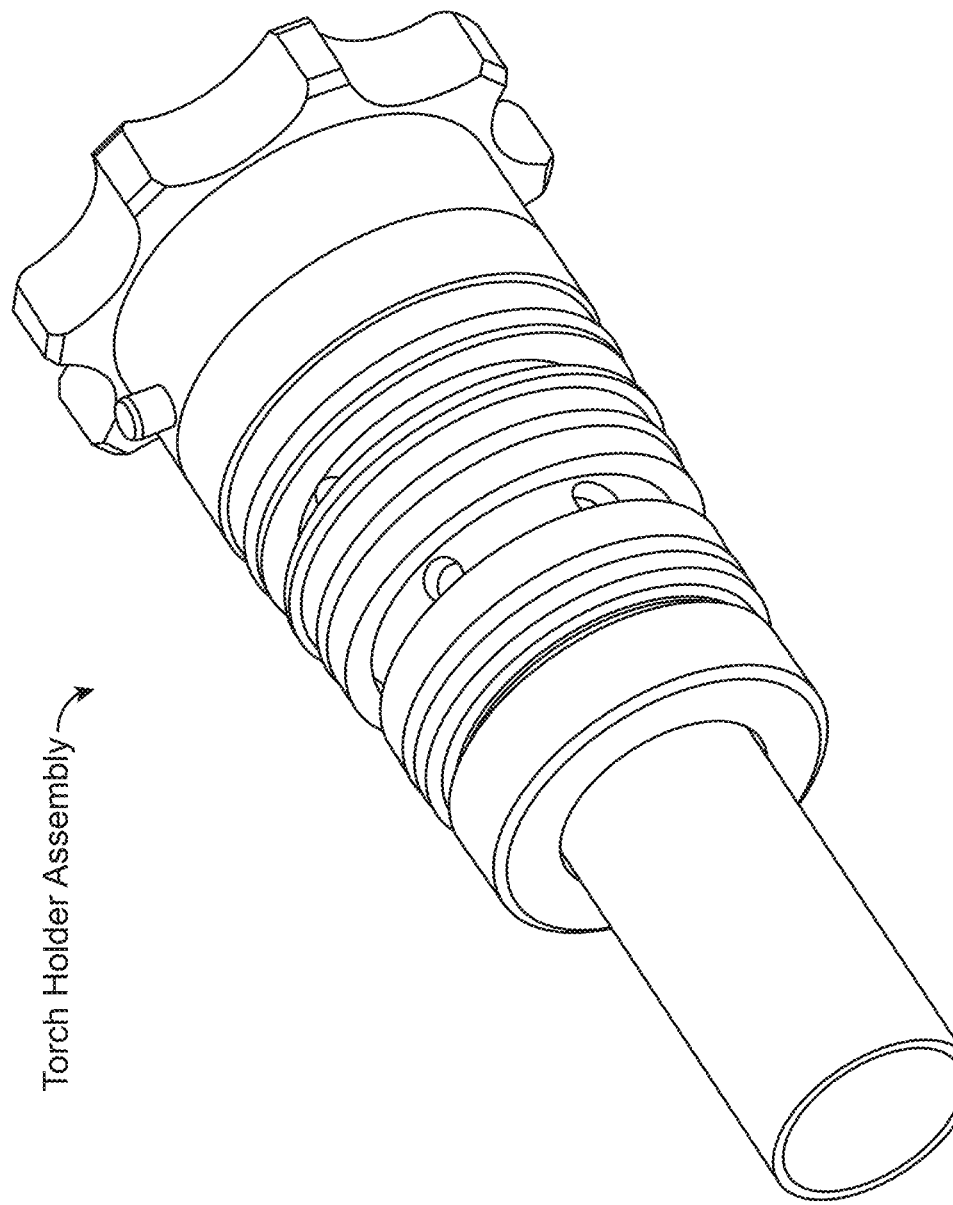
FIG. 7 is a diagram of an exemplary torch holder assembly of the subject application.
Figure 8:
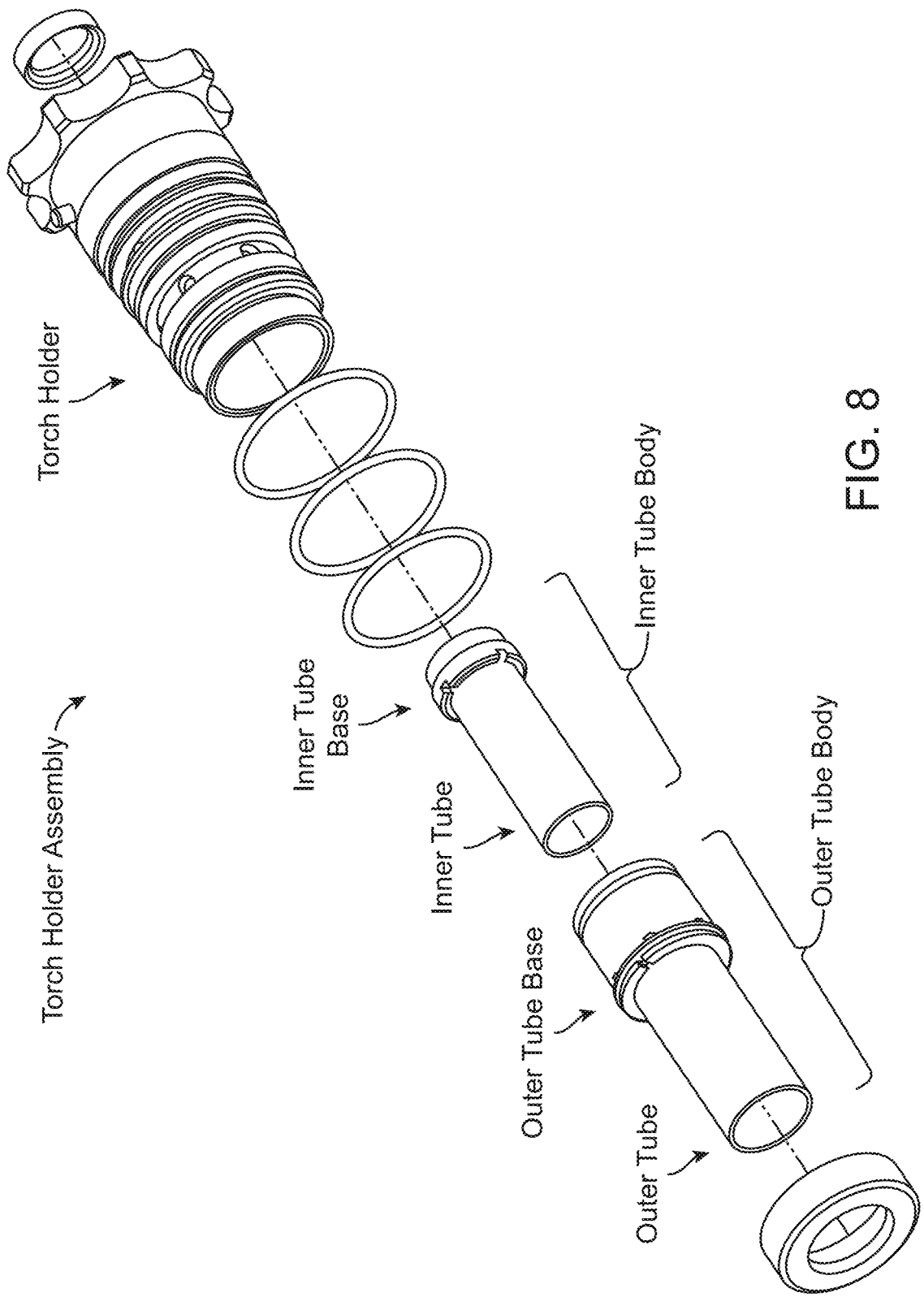
FIG. 8 is an exploded diagram of the torch holder assembly of FIG. 7.

FIG. 7 shows a close up view of the torch holder assembly of FIG. 5. FIG. 8 shows an exploded view of an exemplary torch holder assembly, including an inner torch body comprising an inner tube coupled to an inner tube base, and an outer torch body comprising an outer tube coupled to an outer tube base. The inner base and outer base are received by the torch holder, and are releasable from the torch holder and from their respective tubes.

The ICP torch box may comprise a torch holder assembly that provides a vortex flow and/or is demountable as described in one or more aspects herein. For example, an outer torch body and optionally inner torch body are demountable from a torch holder, as described herein. Alternatively or in addition, an outer tube may be detachable from an outer tube base and/or an inner tube may be detachable from an inner tube base. Alternatively or in addition, the torch holder assembly may be easily removable from the torch box (e.g., by twisting and/or pulling backwards), and may be demounted without the need to remove an ignition electrode from the outer tube.

The ICP torch box comprises an external ignition device, as described in one or more aspects herein. The external ignition device may be positioned outside an outer tube, and upstream of the ICP coil. The external ignition device may comprise two electrodes positioned on opposite sides of the outer torch tube. The mechanism of external ignition may be by electric discharge, such as dielectric barrier discharge as described further herein. In certain aspects, the external ignition devices enables the design and operation of a demountable torch, particularly for ICP-MS analysis where an ignition electrode downstream of the torch is not suitable. The external ignition device of any aspect (or aspects) discussed herein may be combined in the ICP torch box with a torch holder assembly of any aspect (or aspects) discussed herein.

In certain aspects, the ICP torch box comprises an ICP load coil of the subject application. The ICP load coil of any aspect (or aspects) discussed herein may be combined in the ICP torch box with a torch holder assembly of any aspect (or aspects) discussed herein and/or with an external ignition electrode of any aspect (or aspects) discussed herein.

Optionally further, any ICP torch box described above may further comprise a gas supply manifold of any aspect (or aspects) described herein.

In certain aspects, a spray chamber and/or an injector (tube extending from the spray chamber) may be described as part of the torch box, although the spray chamber may be described as part of a sample introduction system to the torch box. In general, injector of the spray chamber delivers sample (e.g., aerolized particles) concentrically into an inner tube (i.e., innermost tube) of the ICP torch, and may be inserted into the inner tube during operation.

In certain aspects the ICP torch box is part of an ICP analyzer. For example, a sample cone of a mass analyzer may be positioned to receive ionized atoms produced from a sample by an ICP plasma of the ICP torch. In such a case, an external ignition device described herein may enable a demountable design of the torch holder assembly as described herein.

Aspects include an inductively coupled plasma (ICP) torch box comprising: a demountable ICP torch holder assembly, an external ignition device that ignites a plasma by dielectric barrier discharge, and/or an ICP load coil comprising an annular fin. The ICP load coil may be 3D printed.

In a specific embodiment, n inductively coupled plasma (ICP) torch box comprising:

(1) a demountable inductively coupled plasma (ICP) torch holder assembly, comprising: an inner torch body comprising an inner tube coupled to an inner tube base an outer torch body comprising an outer tube coupled to an outer tube base, and a torch holder retaining a demountable inner torch base and a demountable outer torch base;

(2) an ICP load coil positioned around the outer tube, comprising: a cylindrical coil, wherein the cylindrical coil comprises an annular fin and wherein the annular fin is contiguous for at least an eighth of a turn of the cylindrical coil, and wherein the ICP load coil predominantly comprises a metal or alloy that has a lower rate of oxidation during operation than copper; and (3) an ignition device for igniting a plasma in an inductively coupled plasma (ICP) torch, the ignition device comprising: a circuit comprising: an oscillator, a first high voltage transformer coupled to a first electrode, a second high voltage transformer coupled to a second electrode, wherein the ignition device is configured to ignite the plasma by dielectric barrier discharge, and wherein the first and second electrodes are positioned on opposite sides of the outer tube and within 5 millimeters of the outer tube.

Torch Holder Assembly

Various embodiments of the subject application relate to torch assemblies and their use, as exemplified in aspects discussed below. Such aspects may be combined in any workable combination).

Aspects of the subject torch assemblies include a demountable ICP torch holder assembly, such as an ICP torch box comprising the torch assembly and methods of use. A demountable torch may be removable from the torch box (e.g., from a gas supply manifold of the torch box) by pulling a torch holder of the demountable torch backward (i.e., opposite the direction gas would flow through the torch during operation). In certain aspects, the demountable torch may be secured by a gas source manifold in the ICP torch box, and may twist out (e.g., to twist a pin of the demountable torch out of a position locked into the gas flow manifold) prior to removing the torch assembly. In certain aspects, the ICP torch box comprises an external ignition electrode as described herein, such that no electrode is inserted into an outer tube of the ICP torch assembly, thereby simplifying the steps of removal of the torch assembly from the torch box (e.g., allowing removal in a single step). Such removal may facilitate maintenance of the ICP torch (e.g., cleaning or replacement of one or more torch tubes).

Alternatively or in addition, a torch holder of the demountable ICP torch assembly may be configured to receive (and therefore allow removal of) at least an outer torch base coupled to an outer tube. Similarly, the torch holder may be configured to receive an inner torch base coupled to an inner tube. Alternatively, the torch holder may be permanently attached (e.g., may be machined as the same piece or adhered together) to the inner tube and/or an inner tube base coupled to the inner tube. The torch assembly may be configured to align the inner tube and outer tube concentrically. O-rings may be used to provide an airtight seal between the inner and/or outer tube base and the torch holder. In certain aspects, the inner tube base and outer tube base may directly reference one another permanently (e.g., may be machined as the same piece or adhered together) or may be configured to join to one another directly by a fastener, such as threads of one of the inner and outer torch base that screws into the other torch base. An inner and outer base that directly reference one another may be removable from the torch holder as a single unit.

The inner tube and/or outer tube described in aspects herein may be of a material such as glass, quartz, or ceramic. The inner tube base and/or outer tube base described in aspects herein may be of a different material, such as metal (e.g., an aluminum alloy).

In certain aspects, the outer torch tube may be detachable from the outer torch base for maintenance (e.g., cleaning or replacement). The outer torch tube may be damaged by chipping, heating, or deposition during operation. The outer torch tube may be less expensive than the outer torch base, this demountable setup reduces cost of maintenance. Similarly, in certain aspects, the outer torch tube may be detachable from the outer torch base for maintenance (e.g., cleaning or replacement). The outer torch tube may be damaged by chipping, heating, or deposition during operation. The outer torch tube may be less expensive than the outer torch base, this demountable setup reduces cost of maintenance.

The torch assembly may be configured to allow an outer gas (also known as a plasma gas) to enter an outer tube of the torch assembly.

One hole, and sometimes two holes, have been used previously for introducing a vortex flow. Often, the holes may be defined by a tube of the same material (e.g., glass, quartz or ceramic) as the outer torch tube and positioned in the side of the torch tube. Such a design may complicate detachment of the torch assembly (e.g., from a gas supply manifold) and/or detachment of the outer torch tube from a torch holder of the torch assembly. Further, such a design may not accommodate several such holes.

In certain aspects, an outer torch body of the torch assembly may comprise a plurality of holes (e.g., three or more holes, such as six holes) positioned and oriented to direct an outer gas into an annular region between the inner and outer tube, and to create a vortex flow therein. While the holes may be radially symmetrical, they may be oriented diagonally (i.e., may not extend radially outward from the axis of a cylinder defined by the outer tube). The holes may be in an outer torch base of the outer torch body. When the outer torch body and inner torch body is retained by a torch holder (e.g., at their respective bases), the holes of the outer torch base may allow fluidic communication from an outer gas inlet of the torch holder to an annular region defined between the inner tube and outer tube. The torch holder may in turn be retained by a gas supply manifold, which provides fluidic communication between an outer gas inlet (e.g., port) of the gas supply manifold and the outer gas inlet of the torch holder. In certain aspects, the outer torch base, torch holder, and gas supply manifold are all comprised primarily of a metal.

Alternatively or in addition, the torch holder may provide fluidic communication for an inner gas (also known as an auxiliary gas) to pass from the gas supply manifold into the inner torch body. Alternatively or in addition, the gas supply manifold may fluidic communication for a carrier gas (also known as a spray chamber gas, or aerosol gas) to flow from a carrier gas inlet (e.g., a port) of the gas supply manifold and into a spray chamber. As such, the gas supply manifold may have a separate port for one or more of a carrier gas, inner gas, and outer gas. Each port may be coupled to a gas source, such as a gas source comprising Argon and/or Helium. In certain aspects, the outer gas may comprise Argon. Alternatively, the outer gas may comprise a gas besides Argon or Helium, such as Nitrogen.

The above described fluidic communication may allow for tubing to be positioned farther from the torch holder assembly (e.g., not directly coupled to the torch holder or outer torch body), enabling the torch holder to be more easily demountable from the torch box (e.g., from a gas supply manifold thereof).

In certain aspects, a demountable ICP torch holder assembly, comprises: an inner torch body comprising an inner tube coupled to an inner tube base, an outer torch body comprising an outer tube coupled to an outer tube base, a torch holder configured to receive the inner torch base and the outer torch base, wherein the inner tube and the outer tube define an annular region when the torch holder retains the inner torch base and the outer torch base.

In certain aspects, the outer tube detaches from the outer tube base and/or the inner tube detaches from the inner tube base.

The torch holder may an outer gas inlet, wherein the outer gas inlet is in fluid communication with the annular region. The outer tube base may define three or more holes (e.g., six holes) positioned to provide fluid communication between the outer gas inlet and the annular region, and wherein the three or more holes are oriented to create a vortex flow. The holes may be positioned close to the plasma such that the vortex flow does not dissipate, and only a low outer gas flow is required. For example, the holes may be within 2.5 cm of an outlet of the inner torch tube. The outer tube may not comprise a taper. Alternatively, the outer tube defines a taper, wherein the taper accelerates the outer gas toward the plasma.

The inner tube base and the outer tube base may each be separately demountable from the torch holder, or may reference one another (e.g., wherein the inner tube base and the outer tube base are permanently joined to each other, wherein the inner torch base and the outer torch base are configured to be connected by a fastener such as a thread).

Wherein the torch holder comprises a thermally conductive element positioned to heat an injector, so as to reduce deposition and/or clogging in the injector.

In certain aspects, a metal or alloy, such as an aluminum alloy, is the predominant material of the torch holder. Wherein the outer tube does not comprise a hole for extending an electrode into the outer tube.

The torch box may further comprise a gas supply manifold configured to receive the torch holder. For example, the torch holder may include a pin to align its position in the gas supply manifold, and wherein twisting the torch holder allows removal of the torch holder from the gas supply manifold. The torch holder may define an outer gas inlet, wherein the outer gas inlet is in fluid communication with the annular region and with an outer gas flow region of the gas supply manifold.

In certain aspects, an inductively coupled plasma (ICP) torch assembly, comprises: an inner tube, an outer tube, and an outer tube base coupled to the outer tube, wherein the inner tube and the outer tube define an annular region, and wherein the outer tube base defines three or more holes positioned to allow an outer gas to pass into the annular region, and wherein the three or more holes are oriented to create a vortex flow.

Figure 9:
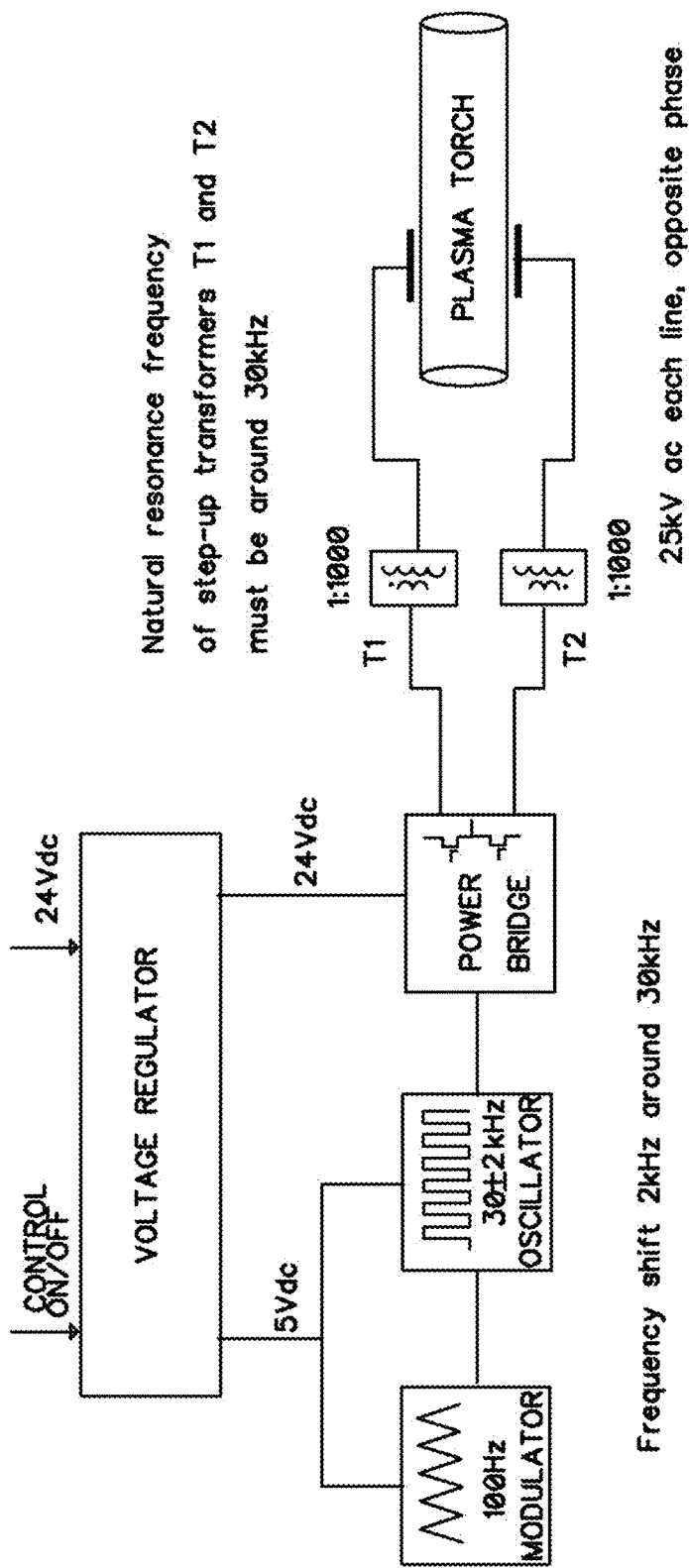
FIG. 9 is a circuit diagram of an exemplary external ignition device of the subject application.

FIG. 9 is a diagram of a cross-sectional view of an exemplary torch holder assembly. As shown, a torch holder retains a torch base. The torch base may be a single workpiece (e.g., a continuous piece of plastic or an inner and outer base that are permanently affixed to one another), or may comprise a separate inner and outer base that can be decoupled from one another. Having an inner base that is separable from the outer base may allow for the inner torch body (the inner base and inner tube) to be separated from the outer torch body for cleaning or replacement. For example, the outer torch may need more regular maintenance due to heat or deposition of material from exposure plasma.

As also shown in FIG. 9, the torch base may comprise one or more outer gas inlets (e.g., at least 2, at least 3, at least 4, such as 6, 8 or 10 outer gas inlets), each communicating with a separate hole that directs an outer gas from a gas supply manifold (not shown) into an annular space between the inner tube and an outer tube of the torch holder assembly.

The holes may be positioned directly adjacent to the outer tube, such that the outer gas is directly injected into the space between the inner and outer tubes. The holes may be angled to arranged to provide a vortex flow.

In certain aspects, the outer tube and inner tube may be permanently affixed to the torch base (e.g., the outer tube to an outer torch base and the inner tube to the inner torch base). For example the outer tube may be affixed to the outer torch base through an adhesive (e.g., a thermally resistant glue). A gap between the outer wall of the outer tube and the torch base (e.g., the outer torch base) allows for an adhesive to join the two, and may allow for expansion of the outer tube and/or the adhesive during heating (e.g., while the torch is operated). In certain aspects, the gap may have a width greater than 0.2 mm, greater than 0.5 mm, or greater 1 mm, such as about 2 mm. This permanent joining and/or gap allows the outer tube to be joined to the torch base without an interference fit. The length of overlap between the outer tube and the torch base may be short, such that a vortex flow of an outer gas injected into the outer torch by the holes has minimal distance during which it may dissipate or lessen before a plasma sustained by the torch. This length may be, for example, less than 10 mm, or less than 5 mm.

External Ignition

While an ICP load coil may sustain a plasma in the ICP torch, an ignition electrode, such as a tesla coil electrode, is typically employed to ignite the plasma by a process described as arc discharge or sparking. Sparking from the ignition electrode may be with a conductive element (e.g., a grounded conductive element) proximal to the plasma, such as the ICP coil. The ICP torch may operate at atmospheric pressure (e.g., between 0.9 and 1.1 atm). In ICP-AES, the electrode may be positioned downstream of the outer torch tube (i.e., downstream in terms of the flow of gas through the torch), as the plasma is directly analyzed by spectroscopy. However, in ICP-MS, the sample cone positioned proximal to the outlet of the outer tube to accept ionized atoms into the mass spectrometer may prevent an ignition electrode downstream of the torch, as the ignition electrode may spark with the sample cone rather than any conductive component proximal to where a plasma would be maintained. This problem has previously been solved by inserting an ignition electrode through the outer torch tube (e.g., downstream of the ICP coil as described in U.S. Pat. No. 4,766,287). However, inserting the electrode through the torch body may prevent the torch assembly from being easily removable for maintenance (e.g., for cleaning or replacement of one or more torch tubes). As such, in certain aspects, the external ignition device and method of the subject application may be combined with the demountable torch described further herein.

External ignition allows for a de-mountable torch having a metal assembly for the insertion/holder and gas feed portion. The inventors found that the mass cytometer ignition method with internal spark electrode was not useable due to the proximity of metal parts in the torch assembly; the spark would fly back to the base of the torch instead of sparking to the sampling interface. The external electrode arrangement positions electrodes out of the way while still having the discharge occurring close to the plasma space. Early successful experiments employed one electrode, the discharge going to the metal base of the torch tube. AC pulses produced with a tesla coil external to the torch may also be sufficient for plasma formation. Inventors also identified a more energetic high voltage AC generator with symmetrical output. This provided reliable ignition as well as repeatability for easy manufacturing.

An external ignition device that ignites a plasma in an inductively coupled plasma (ICP) torch by electric discharge, such as by electrostatic barrier discharge. The external ignition device may be configured to provide an AC current to at least one electrode.

An exemplary external breakdown circuit shown in FIG. 9 comprises an oscillator that produces an alternating current signal with frequency of approximately 30 kHz which is varied within a range of +/−2 kHz about the median value by means of a low frequency (100 Hz) modulator. The modulated signal is then amplified in a power bridge circuit that drives the two output transformers T1 and T2. The transformers T1 and T2 are connected in the circuit in opposite polarity such that their respective output voltages are in phase opposition (180 degrees out of phase with each other). Transformers T1 and T2 operate close to their natural resonance, effectively stepping up the voltage to up to 30 kV, which is then applied to the ignition electrodes attached to the torch assembly. Of note, transformers with a different frequency than 30 kV (e.g., elsewhere in the 1 kV to 100 kV range) may be paired with an oscillator that operates at a similar frequency. The median frequency of the oscillator was chosen to be 30 kHz such as to be at approximate resonance frequency of the step-up transformers T1 and T2 (which are, in principle, identical to each other but may be affected by production tolerances).

Due to production tolerances the actual resonance frequency of the transformer may not be exactly as specified at 30 kHz. However, it is important to drive the transformer with ac current at the transformer's actual resonance frequency in order to attain the maximum output voltage for ignition.

To make sure that the resonance frequency of the transformer is met, a 100 Hz modulator was employed, which applies a triangular ramp signal to a control input of the 30 kHz oscillator, thereby causing the oscillator's frequency to constantly sweep within a range between about 28 and 32 kHz. Each time the natural resonance frequency of the transformer is momentarily matched, the transformer's output voltage, which is applied to the ignition electrodes, increases momentarily to up to 30 kV starting the discharge in the Argon gas column inside the torch. Once initiated, the discharge continues even as the frequency sweeps past the resonance peak. The voltage needed to maintain the discharge is significantly lower than the voltage required to initiate the discharge in the Argon gas.

The ignition circuit is supplied with constant 24 Vdc from the host instrument and its operation is triggered ON/OFF by means of a signal coming from the plasma management system within the instrument.

In this specific embodiment shown in FIG. 9 and discussed above, all internal operation of the ignition module is fixed, no external software control was needed other than on-off operation. However, in other applications it may be desirable to have computer control of the output voltage, modulation frequency and range etc. A physical computer interface providing for such control can be easily added.

Exemplary alternatives to FIG. 9 include one or more of:

Setting a median oscillator frequency of different value, using step-up transformers of different construction.

Absence of low frequency modulation (in the case that the oscillator frequency can be precisely matched to the transformer's resonance, as for example, by providing a trimming potentiometer in the circuit board).

Single-ended output by employing only one transformer and having the second electrode connected to ground. For example, the second electrode could be missing altogether and ground end of the discharge could be provided be some other grounded metal part of the torch.

The ON/OFF control line could be omitted and on-off operation be controlled by switching the 24 Vdc as required.

The above alternatives are not intended to be limiting, but are instead intended to demonstrate some of the aspects that can be modified.

In certain aspects, the external ignition device includes at least one electrode. For example, the external ignition device may include a single external electrode paired with an isolation element (e.g., a torch tube) in the path of the discharge, then the mechanism of ignition may be described as an dielectric barrier discharge (DBD). Similarly, two electrodes positioned on opposite sides of a torch tube, as described herein, would provide ignition by an dielectric barrier discharge (DBD). Dielectric-barrier discharge (DBD) is the electrical discharge between two electrodes separated by an insulating dielectric. In the above aspect of two electrodes positioned on opposite sides of the outer torch tube, the torch tube is the insulating dielectric, and the discharge is across the gas flowing through the torch. More generally, the mechanism may be described as electric breakdown discharge (or electric discharge), and would also describe instances of discharge to a metal component (e.g., grounded component of the ICP torch), such as the ICP coil or a torch tube base. In some cases the mechanism of ignition may be described as electrostatic discharge.

In some aspects, the mechanism of ignition by the external ignition electrode may be described as a glow discharge (e.g., as opposed to an arc discharge). However, as used herein, such glow discharge would be at or around atmospheric pressure, requiring a different external ignition device and operation that if plasma were ignited at low pressure. The plasma density created in by the external ignition electrode may be much lower arc discharge and may more closely resemble that of glow discharge.

The external ignition described herein may be different from ignition schemes that use one or more of arc discharge, high voltage breakdown, a DC current, a Tesla coil, and/or direct contact between the ignition electrode and the gas to be ignited into a plasma.

In certain aspects, an external ignition device for igniting a plasma in an ICP torch comprises a circuit comprising: an oscillator, a first high voltage transformer coupled to a first electrode, and optionally a second high voltage transformer coupled to a second electrode, wherein the ignition device is configured to ignite the plasma by dielectric barrier discharge. The plasma may be ignited at atmospheric conditions (e.g., within 10% of 1 atm), or at least above 100 Torr. The external ignition device may configured to provide an alternating output voltage to at least one electrode, such as a first and second electrode, e.g., wherein the first and second high voltage transformers are connected to the circuit at opposite polarity. The device may provide a voltage differential between the first and second electrodes of at least 1 kV, such as between 2 kV and 100 kV, between 5 kV and 50 kV, or between 20 KV and 40 kV. A maximum output voltage of a high voltage transformer of the circuit each between 2 kV and 50 kV, such as between 10 kV and 40 kV. In certain aspects the maximum voltage of a high voltage transformer of the circuit is less than 1 MV, such as less than 200 kV. In certain aspects the alternating voltage is at a frequency is less than 1 MHz, such as between 5 kHz and 100 kHz or between 20 kHz and 40 kHz. The alternating output voltage and/or its frequency is sufficient to ignite a plasma at atmospheric pressure (e.g., within 10% of 1 atm).

The external ignition device may be configured or operated to ignite a plasma through electric breakdown discharge, such as by dielectric barrier breakdown. The plasma may be ignited through capacitance between a portion of the outer torch body next to the first electrode and a portion of the outer torch body next to the second electrode.

In certain aspects, the external ignition device may not be configured or operated to ignite a plasma through sparking, or at least through arcing (e.g., arc discharge). The external ignition device may not comprise a tesla coil.

The device may comprise two electrodes. The electrodes may be positioned outside an outer torch, such as wherein the electrodes are positioned to be within 5 millimeters or within 3 mm of an outer torch wall of an ICP torch. The two high voltage transformers are connected to the circuit in opposite polarity such that their respective output voltages are in phase opposition. The two high voltage transformers may have a maximum voltage output of between 5 kV and 100 kV. The circuit further comprises a voltage modulator configured such that the oscillator periodically meets the natural resonance frequency of each of the first and second high voltage transformers. The circuit is at a fixed alternating output voltage and frequency. Alternatively, at least one of the output voltage and its frequency is controllable by a computer external to the external ignition device.

The device may be part of an ICP torch, wherein the electrodes are positioned outside an outer torch body of the ICP torch. The ICP torch may comprise an inner torch body, at least a portion of the outer torch body is concentric with the inner torch body, and the first electrode and the second electrode are positioned such that an axis through the first electrode and the second electrode intersects the portion of the outer torch body.

ICP Load Coil

Aspects of the subject application include ICP load coil (ICP coil) for maintaining a plasma (e.g., when operated at an RF frequency AC current). The ICP load coil may be cylindrical, meaning is in the shape of a spiral that defines a cylinder. Often such as a coil takes 3 turns. The ICP load coil may be positioned in a torch box to surround an outer torch tube.

Standard cylindrical ICP load coils are made from copper, and are shaped as either solid wire or hollow (a tube). In contrast, aspects of the ICP load coil of the subject application may include a material other than copper and a shape other than a solid wire or hollow tube. The material and or shape of the ICP load coils discussed herein may reduce aging of the coil, e.g., may reduce heating, oxidation and/or deformation of the coil during operation to maintain a plasma.

In certain aspects, the ICP coil may be 3D printed. Alternatively, the ICP coil may be machined or cast.

In certain aspects, the ICP coil may comprise an annular fin. An annular fin is understood to be a fin that widens as it extends from a center axis. Such a fin may be difficult to form machining metal, as it may require deformation (stretching) to widen in this way when bent to form a coil. As such, the ICP coil may comprise a 3D printed annular fin. The annular fin may increase cooling of the ICP coil during operation (thereby also reducing oxidation). The annular fin may extend along at least an eighth of a turn of the ICP coil, and may extend along 2 or more turns. The inventors have found that a continuous fin does not reduce the efficiency of the ICP coil. Metrics such as frequency of operation, inductance, and maintenance of the plasma remain unchanged compared to designs with gaps in the annular fin. The lack of gaps (or at least of frequent gaps) in the annular fin may further provide structural stability (e.g., to resist deformation during operation as described herein). One of skill in the art may be concerned that the current would travel partly along the outside of a coil with a continuous annular fin and thereby reduce ICP efficiency or hamper operation of the coil.

The material and/or shape of the ICP coil may improve structural stability of the coil, allowing for a more resilient manufacturing process and/or increased lifetime. For example, the ICP coil of the subject application may survive operation of at least 5,000 hours, at least 10,000 hours, at least 20,000 hours, or at least 50,000 hours (e.g., without breaking, reducing ICP efficiency by more than 10%, reducing signal detected by a mass analyzer by more than 10%, or falling outside a frequency or induction tolerance).

In certain aspects, the ICP coil may be an alloy, such as an aluminum alloy. The alloy may lend itself to 3D printing. Alternatively or in addition, the alloy may have a number of additional properties compared to copper and discussed herein.

In certain aspects, an ICP load coil is a cylindrical coil comprising an annular fin. The annular fin may be contiguous for at least an eighth of a turn of the cylindrical coil, such as along at least 2 turns of the coil. The ICP load coil may predominantly comprise a metal or alloy that has a lower rate of oxidation during operation, or during the lifetime of the instrument, than copper. The annular fin may be substantially planar. An inner portion of the ICP load coil is thicker than an outer portion of the ICP load coil. The inner portion may define a round cross section and the outer portion is the annular fin. An inner portion of the ICP load coil may have a greater minimum diameter than the outer portion of the ICP load coil. The ICP load coil may be solid. The ICP load coil may not comprise multiple annular fins. One or more annular fins may be present along the majority of three turns of the ICP load coil. A distance from the innermost portion of the annular fin to the outermost portion of the annular fin may be at least twice the thickness of at least a portion of the annular fin.

In certain aspects, the ICP coil may be less than 10 cm, such as less than 5 cm long (along its cylindrical axis).

The metal or alloy may be an aluminum alloy. The metal or alloy may have at least one of a lower conductivity than copper, a lower melting temperature than copper, or a lower ductility than copper. The ICP load coil may be formed by 3D printing the metal or alloy, or alternatively by casting or machining. The metal or alloy is an alloy that reduces a deformation during operation compared to copper than if the ICP load coil did not comprise the annular fin. The metal or alloy is an alloy that reduces a deformation compared to copper, such as deformation perpendicular to the axis of the cylinder defined by the coil and/or wherein the deformation is along the axis of the cylinder defined by the coil.

The ICP load coil may comprise a first portion closest to the longitudinal axis of the cylindrical coil, wherein the ICP load coil comprises a second portion farthest from the longitudinal axis of the cylindrical coil, wherein the first portion is characterized by a first thickness, wherein the first thickness is measured perpendicular to a first axis parallel to the longitudinal axis, wherein the second portion is characterized by a second thickness, wherein the second thickness is measured perpendicular to a second axis parallel to the longitudinal axis, wherein the first thickness is greater than the second thickness.

Sample Introduction

Aspects of the invention include a sample introduction system, such as a particle (e.g., cell or bead) introduction system or a laser ablation system. A particle introduction system for mass cytometry may include multiple components, such as a sample holder, probe for accessing a sample in the sample holder, and/or sample introduction fluidics for introducing the sample (e.g., a suspension of cells) to a spray chamber upstream of an ICP torch box. In certain aspects, the sample holder may be configured to hold a plurality of samples, such as at least 4, at least 8, or at least 12 samples. The sample holder may be movable to present a sample to the probe (e.g., may be a carousel). Automated acquisition of multiple samples may take hours. As such, aspects of the subject application include sample introduction systems for maintaining a suspension of cells. Such systems may comprise elements used in mixing applications outside of flow cytometry, such as those described by Al-Halhouli, Ala'aldeen, et al. in "Passive micromixers with interlocking semi-circle and omega-shaped modules: Experiments and simulations." (*Micromachines* 6.7 (2015): 953-968). In certain aspects, the radius of the turn and the speed of flow of sample through the loop provides a low Dean number (i.e., turbulent flow).

In certain aspects the sample introduction fluidics may include a sample loop in direct or indirect fluidic communication with the probe and the spray chamber. The sample loop may comprise a plurality of turns (e.g., a spiral defining a cylinder). The axis of the cylinder defined by the spiral may be oriented horizontally (e.g. within 15 degrees of perpendicular to the axis of gravity) to reduce the portion of the loop that the cells (or other particles) may settle. Optionally further, the sample loop may be positioned around a cylindrical agitator in contact with the loop, wherein the agitator maintains a suspension of particles in the loop during transport to the spray chamber.

Sample introduction fluidics may be coupled to one or more reservoirs. The reservoirs may include a waste reservoir, a cell acquisition solution reservoir, a wash solution reservoir, and/or a water reservoir. The sample introduction fluidics may comprise a valve system, such as a rotary valve system, that directs fluid flow from the reservoirs and a sample tube (sample loop). As described herein, sample may be directed through a nebulizer, spray chamber and then injector into an ICP plasma, at which stage particles in solution (e.g., cells and/or beads) are atomized and ionized prior to analysis by an analyzer (e.g., a simultaneous mass analyzer). In certain aspects, the injector is a heated injector. A description of a heated injector and cell acquisition solution is provided by US patent publication number US20190317082, which is incorporated herein by reference. In certain aspects, the cell acquisition buffer may comprise a salt in solution, wherein the salt is free of carbon and free of heavy metal (e.g., or any element having an atomic mass greater than 80).

The sample introduction system may comprise at least two syringes that alternate between wash and sample introduction functions. For example, a first pump may function to draw sample, beads, wash solution or cell acquisition solution into the sample loop. A second pump a multi-port valve that connects the syringe to the waste bottle, the cell acquisition solution reservoir, and the switching valve. Its primary function is to push sample, beads, was solution, and/or cell acquisition solution from the sample loop to the nebulizer and to push cell acquisition solution directly from the reservoir bottle to the nebulizer.

The sample introduction system may comprise at least two rotary valves, such as a selector valve and a switching valve. The selector valve may have ports connected to the probe, to the reservoirs, and/or to an empty port that is used to draw in air bubbles. The position of the selector valve may determines where the first pump draws from. A switching valve may switch the sample loop between the load and inject positions. When the switching valve is in the load position, the sample loop can be filled via the fill pump. In the inject position, the sample loop is in line with the nebulizer and its contents can be pushed to the nebulizer via the second pump. The first pump may be a fill pump. The second pump may be a push pump.

Figure 10:
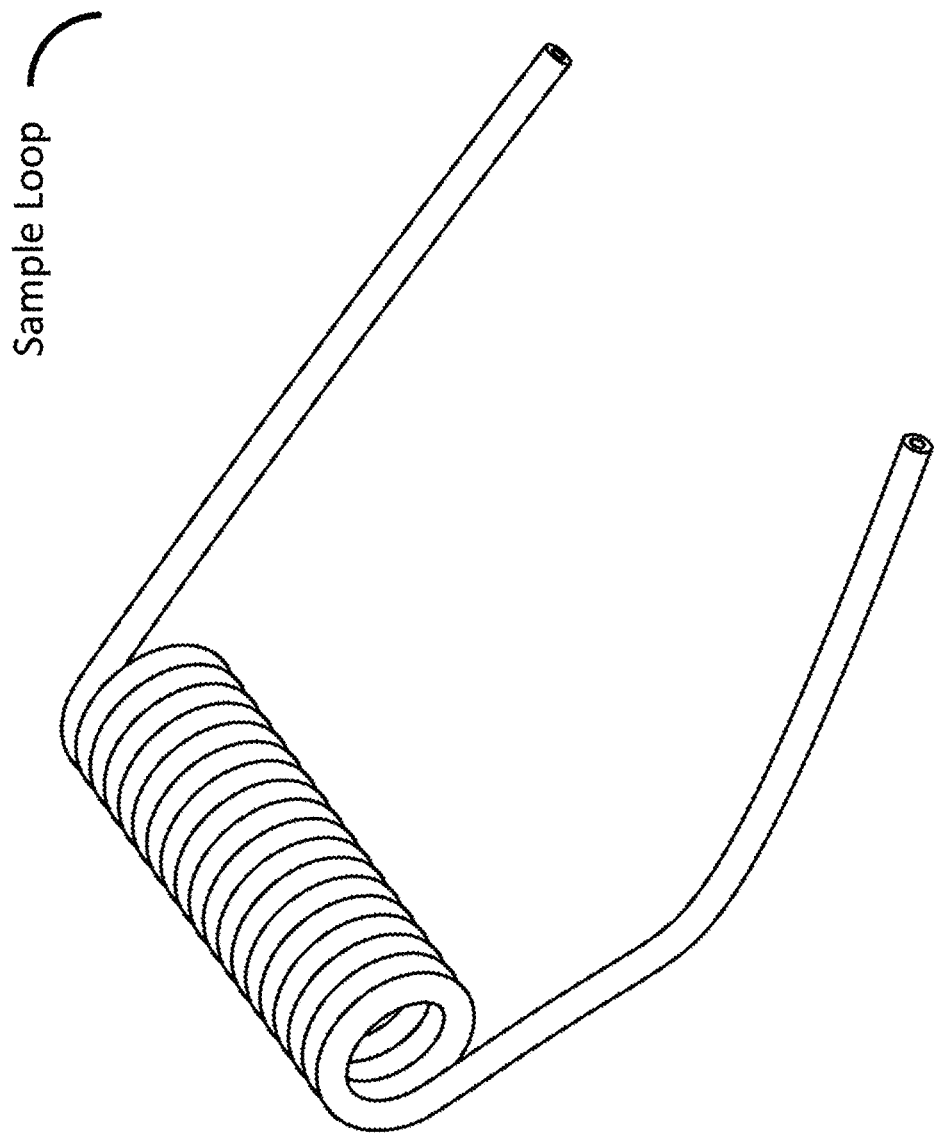
FIG. 10 is a diagram of an exemplary sample loop of a sample introduction device of the subject application.

FIG. 10 is a diagram of an exemplary sample loop of a sample introduction device of the subject application.

Figure 11:
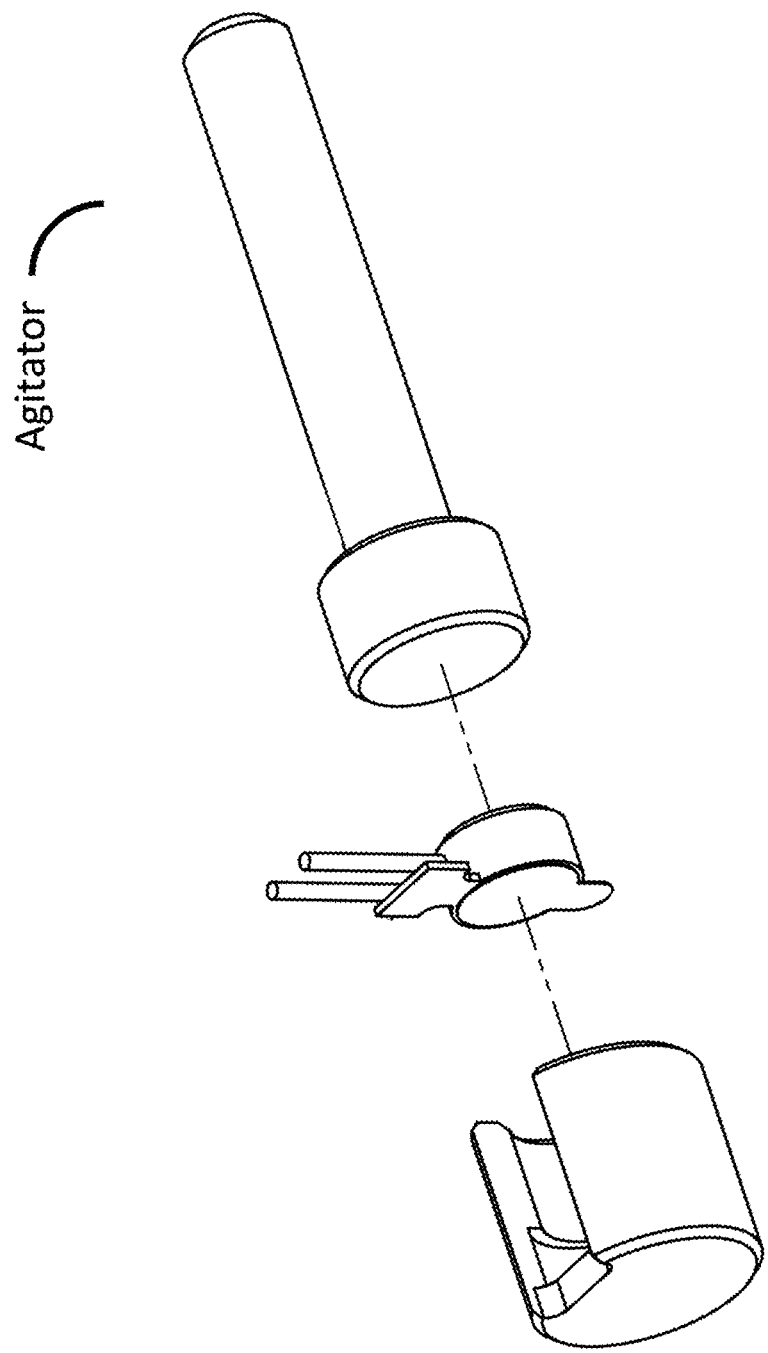
FIG. 11 is a diagram of an agitator for the sample loop of FIG. 10.

FIG. 11 is a diagram of an agitator for the sample loop of FIG. 10. The spiral of the sample loop of FIG. 10 may be fitted around the cylinder of the agitator of FIG. 11.

The component of FIG. 10 or 11 may be within the sample introduction fluidics shown in FIG. 2.

Figure 12:
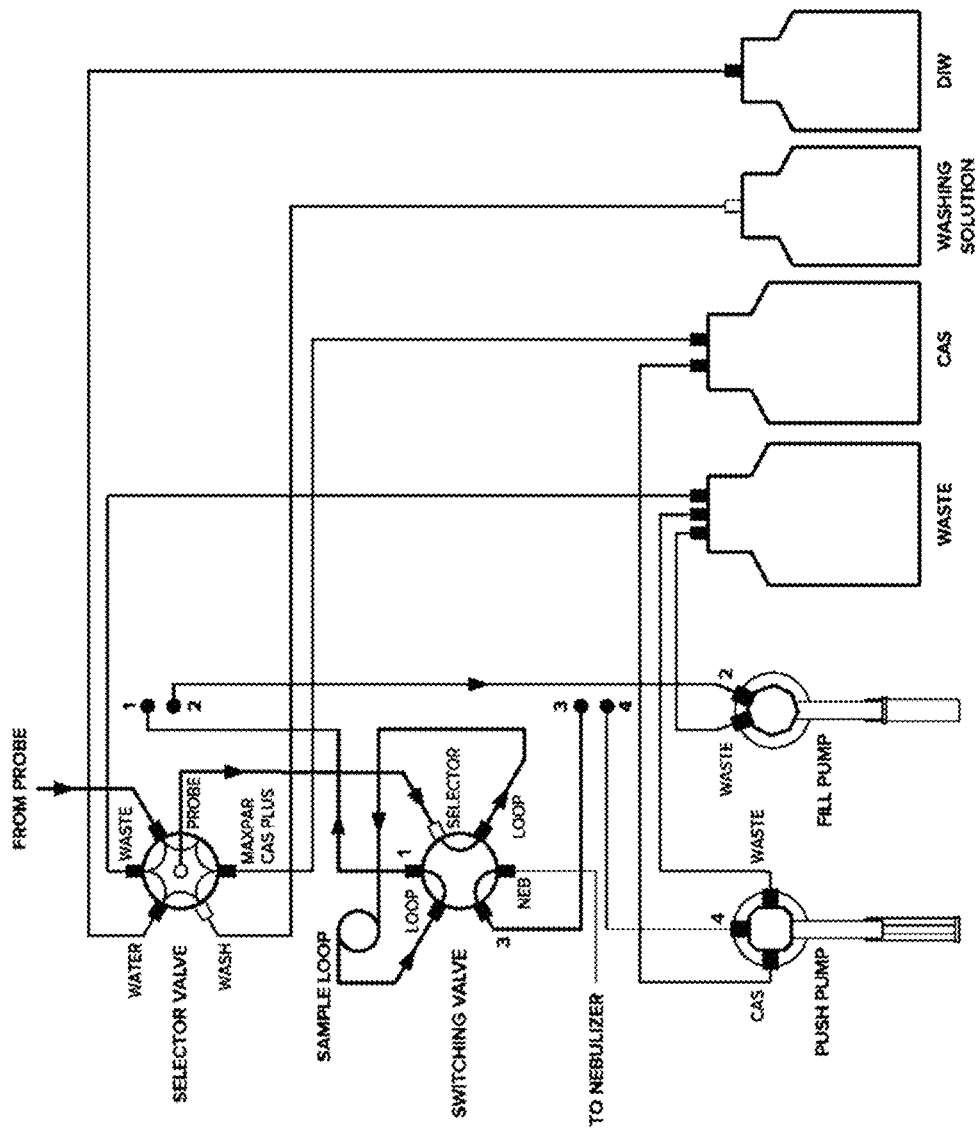
FIG. 12 is a diagram of sample introduction fluidics during sample loading.
Figure 13:
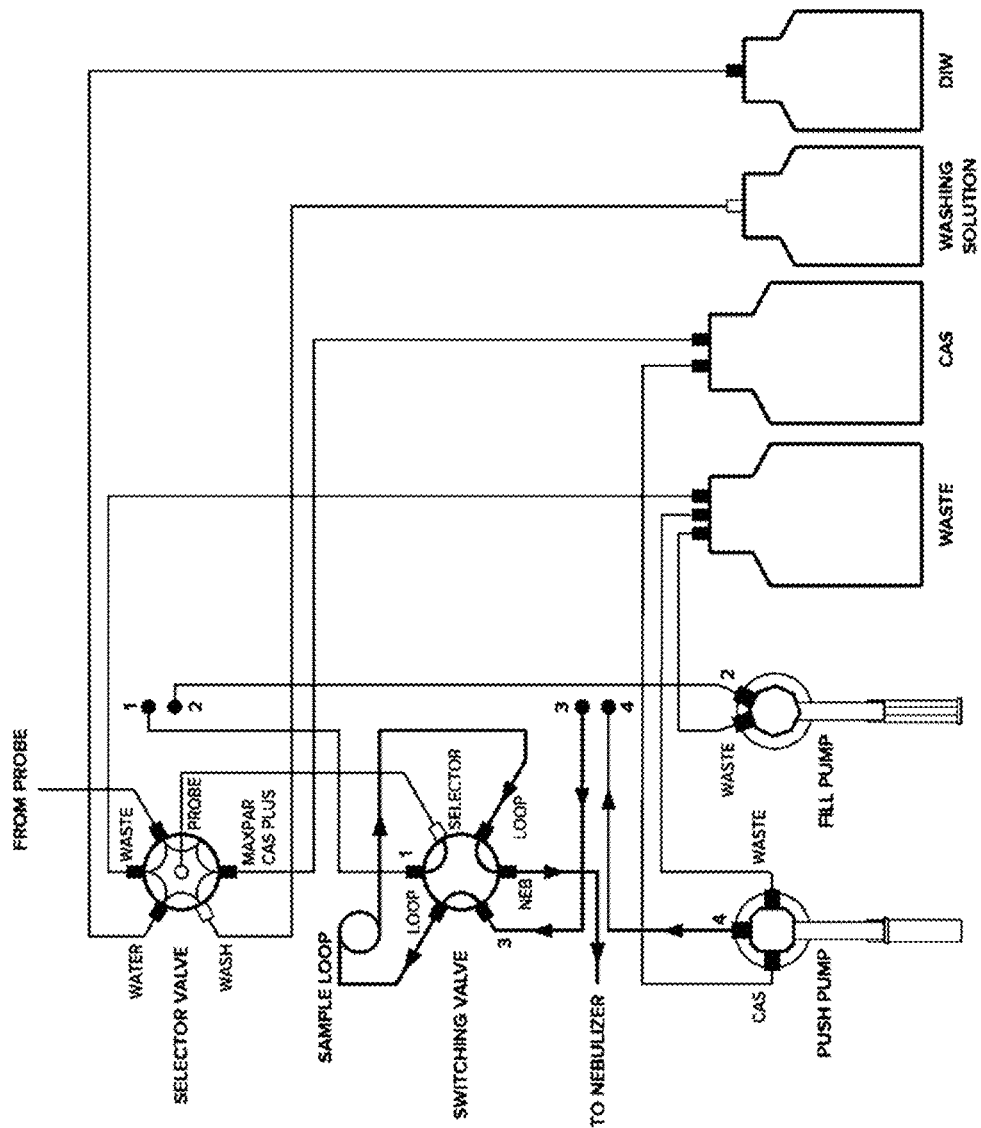
FIG. 13 is a diagram of sample introduction fluidics during sample injection.
Figure 14:
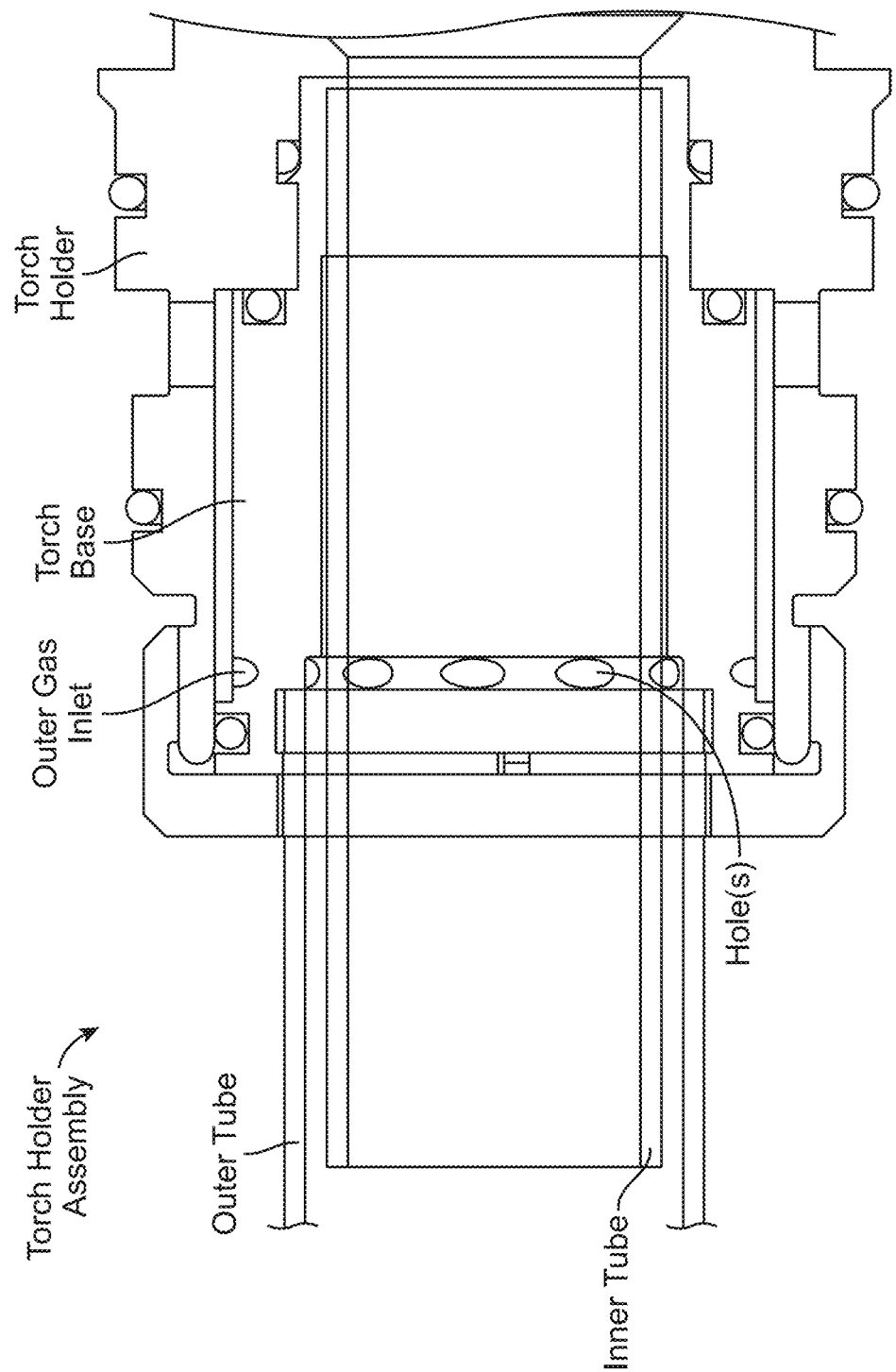
FIG. 14 is a diagram of an exemplary cross section of the torch holder assembly of FIG. 7.

Cell samples in the carousel may be aspirated via the first pump. For example, the sample may be drawn in through the probe towards a selector valve, and then into the sample loop with a switching valve in the load position as shown in FIG. 12. Once sample is loaded into the sample loop, the switching valve may be switched to the inject position and sample pushed to the nebulizer via the first pump as shown in FIG. 13. Cell acquisition solution may be is used as a carrier to push sample to the injector and into the system. An air bubble may be loaded in between the cell acquisition solution and the sample to prevent mixing at the interface between the two.

In certain aspects, the sample loop defines a tightly wound sample loop based on a tight radius of curvature to achieve a low Dean number as described in the 2015 Micromachines article. The sample loop may be aligned to the axis of rotation horizontally so the flow of cells (or particles) experience the least amount of settling time (at the lower end of the loop) due to gravity. As an additional encouragement for preventing the cells from settling within the sample loop, an agitator (vibrating rod) may be used. In contrast to uses in other application, however, the vibration does not settle and pack material while it conveys but simply adds agitation to the flow in order to maintain cell suspension within the carrier fluid. This is akin to having a summer student tapping the sample loop periodically, which works equally well and less costly.

While the sample introduction device may be used in combination with an ICP analyzer, it may alternatively be used or combined with any particle based analysis system, such as flow cytometry.

A sample introduction device of the subject application may comprise a sample loop wherein the sample loop makes at least 3 turns. The turns may be around the cylindrical agitator. The sample loop may forms a spiral comprising at least 5 turns. The spiral may define a cylinder with an axis within 15 degrees from perpendicular to the axis of gravity.

The sampling system and methods of use thereof (e.g., execution by a computer readable medium) may increase productivity with built-in clog detection, automated declogging (i.e., unclogging), and/or shutdown.

In certain aspects, the sample system performs as part of a pellet resuspension workflow, and prior to loading samples. During mixing, a probe line and fill pump may work together to act like a pipette, aspirating and dispensing a volume (e.g., between 25 and 250 µL) multiple times within a tube. A user may select a mixing force value (e.g., between 1 and 10) to define how fast this volume is ejected into the sample tube (e.g., with 1 representing the lowest mixing force and 10 representing the strongest). This parameter may be set to a default value (e.g., 5).

During sample acquisition, the probe line may stir the sample to prevent cells from settling. A user may select a stirring speed value (e.g., between 0 and 9) to define how fast the probe line spins (e.g., where 0 turns off the stirring and 9 is the fastest speed). This parameter may be set to a default value (e.g., 5). During acquisition, the inside and/or outside of the probe line may be washed when a pre-wash cycle is selected by the user or otherwise executed by a computer readable medium.

A default sample loop vibrations setting may help mitigate cell settling within the sample loop.

The device may further comprise a nebulizer in fluid communication with the sample loop. The nebulizer may be in fluid communication with a spray chamber. The spray chamber may be configured to pass on particles to an injector. The device may comprise a sample holder configured to hold one or more samples. The sample holder may be configured to retain a plurality of tubes, e.g., wherein the sample holder is configured to cool the plurality of tubes. The device may comprise a plurality of pumps, valves, reservoirs, and/or tubes configured to transfer a suspension of cells, from a tube presented by the sample holder to a probe, through the sample loop, and out of the nebulizer. The device may comprise a pressure sensor configured to detect a drop in pressure when the probe is clogged with one or more particles, and optionally further a computer readable medium storing a plurality of instructions that when executed control a processor to operate the sample introduction system, e.g., wherein the plurality of instructions comprise automatically reversing a flow (or adjusting a pressure, such as increasing a pressure) when a clog is detected in the probe, thereby declogging the probe. The processor may operate the sample introduction system to resuspend cells in a tube prior to transferring the cells.

The computer readable medium of the subject application may include an autosampler module, which may operate the system described herein to automate clog detection and removal workflows. Aspects of the subject application include one or more of the automated method steps below and a computer readable medium (e.g., of a sample introduction system as described herein, or a mass cytometry system comprising such a sample introduction system) configured to execute such steps. There may be at least 2 pressure sensors in the sample introduction fluidics, such as a first sensor on a push pump and a second sensor on a fill pump (such as the push and fill pumps shown in FIGS. 12 and 13). During sample injection, readings may be from the push pump (e.g., at least once every minute, such as once every 5-6 sec). If the average pressure in a reading, or for a predefined number of consecutive readings (e.g., 2 or more readings, 3 or more readings, 5 or more readings, such as 5 readings) reaches a set threshold, a clog may be detected (e.g., and reported to a user). Sample acquisition (e.g., including sample injection) may then be paused and an automatic unclogging routine initiated.

The unclogging routine may include switching from injection mode to load mode, which enables the push pump to be used to flush the nebulizer while the sample in the sample loop remains undisturbed. An initial attempt to remove the clog may be done by pulse aspirating and flushing at high flow (e.g., for about 1-2 min). If the clog is not removed, the a clog identification workflow may be run (e.g., in which the 2 pressure sensors are used to determine whether the clog is in the sample loop or downstream of the sample loop, for example, in the nebulizer line or the nebulizer). The unclogging procedure may then focus on the location of the clog. During the unclogging procedure, a flow rate level and/or pulse rate (e.g., in the sample introduction fluidics, such as at a probe as described herein) may be increased. In certain aspects, a declogging pressure (e.g., input by a user) may be applied in any of the above steps that increase a pressure, flow or pulse rate. For example, the declogging pressure may be more than 5 psi, more than 10 psi, more than 15 psi, such as between 5 and 40 psi, or between 10 and 20 psi. In certain aspects, a predefined maximum number of clogging events (e.g., input by a user) may trigger an end to sample acquisition.

If the clog is successfully removed using the automated workflow, acquisition may be resumed. If the clog cannot be removed using the automated workflow, acquisition may be stopped, and the sample is returned to the sample tube (if Recover Sample is specified in the acquisition template). The clog may then be removed manually (e.g., a user may be instructed by the software to perform manual unclogging).

ICP Analyzers

An ICP analyzer of the subject application may include any ICP torch box described herein and coupled to an atomic analyzer, such as an MS or AES. The analyzer may be a simultaneous mass analyzer, such as a TOF-MS or magnetic sector MS. The ICP analyzer may be a mass spectrometer or imaging mass spectrometer. The ICP analyzer may be operated to provide an outer gas flow of less than 20 L/min. The ICP analyzer may ignite a plasma by dielectric barrier discharge under atmospheric conditions. The ICP analyzer may be used to analyze a biological sample, such as mass tagged cells or tissue section. In certain aspects, the ICP analyzer may be used to analyzer a non-biological sample.

System Monitoring Devices

In certain aspects, a mass cytometry system or sample introduction system as described herein further includes a system monitoring device configured to communicate system run data, such as one or more settings described herein and/or real-time measurements, to a database. The device may operate independently of a computer used to operate the system, or may be in communication with such a computer. Alternatively or in addition, the computer may performed the functions described herein for the device. The device may be a wireless device. The database may comprise system run data from separate systems in geographically distinct locations. The device may communicate with the database through a wireless router.

In certain aspects, settings may be selected from any parameter or value entered by a user. In certain aspects, real-time measurements may include measurements internal to the system or measurements taken by environmental sensors (e.g., measurements of humidity, pressure and/or temperature external to the system). Real-time internal measurements may include one or more of clogging events (e.g., data directly from pressure sensors or frequency of clogs), flow rates (e.g., of sample fluid, or one or more gases described herein such as a nebulizer gas, carrier gas, inner gas, and/or outer gas), temperature of one or more components (e.g., within a torch assembly or of the ICP load coil), a voltage of a mass detector of the system, a current of one or more cones (e.g., a sampling cone and/or skimmer cone downstream of an ICP torch), a frequency or power an ICP load coil is operated at, a mass signal from element standard beads, a mass detector signal (e.g., a detector signal above a predetermined threshold that may indicate damage or wearing of the detector, cell events), an amount or pressure of gas in a reservoir (e.g., gas tank or dewer supplying a gas to the system), system run times, and so forth.

When a laser ablation system (e.g., for tissue imaging) is configured to deliver laser ablation plumes to a mass cytometer of the subject application (e.g., in place of suspended cells or beads), one or more additional settings and/or real-time measurements associated with the laser ablation system may be provided. For example, laser ablation settings (e.g., power, operating voltage, operating frequency, operating mode, and/or power dissipation), ablation chamber fluidics parameters (e.g., a carrier and/or sheath gas flow rate for delivering ablation plumes to a mass cytometer described herein), humidity internal to the laser ablation fluidics, laser ablation plume width as measured by a mass detector, and so forth.

In certain aspects, the system run data from one or more system runs on the same system may be used to identify preventative maintenance needed on that system. At such point, a user may be notified of the need for such maintenance (e.g., may be prompted to schedule such maintenance). Maintenance may be tuning of the instrument, cleaning the instrument (e.g., cleaning of sample introduction fluidics, a torch body or tube thereof, or of a sampling cone downstream of the ICP torch), or replacement of certain components (e.g., of a laser, mass detector, gas reservoir, torch body or tube thereof, nebulizer or another element of the sample introduction fluidics described herein, and so forth).

Utility

Aspects of the subject systems and methods may provide for a longer lifetime of ICP components, easier operation by the user, and/or reduced maintenance or running cost. For example, the ICP load coil aspects described herein may have improved lifetime compared to a traditional coil. The demountable torch described herein allows for easy maintenance and low cost replacements (e.g., easy access to the torch tubes which may be decoupled from the larger assembly to be replaced). The vortex flow of torch assembly may reduce the flow of outer gas needed to maintain a plasma. The external ignition electrode may enable the demountable torch and/or may have a longer lifetime than an electrode inserted into the torch body. In general, a longer lifetime may be at least twice the lifetime, or at least five times the lifetime, before a component breaks or becomes significantly damaged (e.g., operating at less than 90%, or less than 80% of efficiency than if it were replaced, wherein efficiency is the energy needed to operate the device or the strength of signal detected by an analyzer downstream of the ICP). The sample introduction system described herein may increase user walk-away time, and enable automated sample introduction of a plurality of samples.

What is claimed is:

1. An inductively coupled plasma (ICP) torch box comprising:
   a demountable ICP torch holder assembly;
   an ICP load coil comprising an annular fin, wherein the load coil is a cylindrical coil, and the annular fin is contiguous for at least an eighth of a turn of the cylindrical coil; and
   an external ignition device that ignites a plasma by dielectric barrier discharge.

2. An inductively coupled plasma (ICP) torch box comprising:
   (a) a demountable inductively coupled plasma (ICP) torch holder assembly, comprising:
   an inner torch body comprising an inner tube coupled to an inner tube base;
   an outer torch body comprising an outer tube coupled to an outer tube base;

a torch holder retaining a demountable inner torch base and a demountable outer torch base;

(b) an ICP load coil positioned around the outer tube, comprising:

a cylindrical coil;

wherein the cylindrical coil comprises an annular fin;

wherein the annular fin is contiguous for at least an eighth of a turn of the cylindrical coil;

wherein the ICP load coil predominantly comprises a metal or alloy that has a lower rate of oxidation during operation than copper;

(c) an external ignition device for igniting a plasma in an inductively coupled plasma (ICP) torch, the ignition device comprising:

a circuit comprising:

an oscillator;

a first high voltage transformer coupled to a first electrode;

a second high voltage transformer coupled to a second electrode;

wherein the ignition device is configured to ignite the plasma by dielectric barrier discharge; and wherein the first and second electrodes are positioned on opposite sides of the outer tube and within 5 millimeters of the outer tube.

3. A demountable inductively coupled plasma (ICP) torch holder assembly, comprising:

an inner torch body comprising an inner tube coupled to an inner tube base;

an outer torch body comprising an outer tube coupled to an outer tube base; and a torch holder configured to receive the inner tube base and the outer tube base;

wherein the inner tube and the outer tube define an annular region when the torch holder retains the inner tube base and the outer tube base, and wherein:
  (a) the outer tube detaches from the outer tube base,
  (b) the inner tube detaches from the inner tube base,
  (c) the torch holder defines an outer gas inlet, the outer gas inlet is in fluid communication with the annular region, the outer tube base defines three or more holes positioned to provide fluid communication between the outer gas inlet and the annular region, and the three or more holes are oriented to create a vortex flow,
  (d) the inner tube base and the outer tube base are permanently joined to each other,
  (e) the torch holder comprises a thermally conductive element positioned to heat an injector,
  (f) a metal is the predominant material of the torch holder,
  (g) an aluminum alloy is the predominant material of the torch holder, or
  (h) the torch holder assembly further comprises a gas supply manifold configured to receive the torch holder, the torch holder comprises a pin to align its position in the gas supply manifold, and twisting the torch holder allows removal of the torch holder from the gas supply manifold.

4. The torch holder assembly of claim 3, wherein the outer tube detaches from the outer tube base.

5. The torch holder assembly of claim 3, wherein the inner tube detaches from the inner tube base.

6. The torch holder assembly of claim 3, wherein the torch holder defines the outer gas inlet, the outer gas inlet is in fluid communication with the annular region, the outer tube base defines three or more holes positioned to provide fluid communication between the outer gas inlet and the annular region, and the three or more holes are oriented to create a vortex flow.

7. The torch holder assembly of claim 6, wherein the outer tube base defines six holes.

8. The torch holder assembly of claim 6, wherein the holes are within 2.5 cm of an outlet of the inner tube.

9. The torch holder assembly of claim 3, wherein the outer tube does not comprise a taper.

10. The torch holder assembly of claim 3, wherein the inner tube base and the outer tube base are each separately demountable from the torch holder.

11. The torch holder assembly of claim 3, wherein the inner tube base and the outer tube base are permanently joined to each other.

12. The torch holder assembly of claim 3, wherein the inner tube base and the outer tube base are configured to be connected by a fastener.

13. The torch holder assembly of claim 3, wherein the torch holder comprises the thermally conductive element positioned to heat the injector.

14. The torch holder assembly of claim 3, wherein the metal is the predominant material of the torch holder.

15. The torch holder assembly of claim 3, wherein the aluminum alloy is the predominant material of the torch holder.

16. The torch holder assembly of claim 3, wherein the outer tube does not comprise a hole for extending an electrode into the outer tube.

17. The torch holder assembly of claim 3, wherein the torch holder assembly further comprises the gas supply manifold configured to receive the torch holder, the torch holder comprises the pin to align its position in the gas supply manifold, and twisting the torch holder allows removal of the torch holder from the gas supply manifold.

18. The torch holder assembly of claim 17, wherein the torch holder defines the outer gas inlet, wherein the outer gas inlet is in fluid communication with the annular region and with an outer gas flow region of the gas supply manifold.

19. The torch box of claim 1, wherein the demountable ICP torch holder assembly comprises:

an inner torch body comprising an inner tube coupled to an inner tube base, an outer torch body comprising an outer tube coupled to an outer tube base, and a torch holder retaining a demountable inner torch base and a demountable outer torch base.

20. The torch box of claim 2, wherein the outer tube is reversibly detachable from the outer tube base.

* * * * *